United States Patent [19]

Setoi et al.

[11] Patent Number: 4,916,152

[45] Date of Patent: Apr. 10, 1990

[54] PYRROLIDINE DERIVATIVES AS ANTIASTHMATICS

[75] Inventors: Hiroyuki Setoi; Hideo Hirai; Hiroshi Marusawa; Akio Kuroda; Hirokazu Tanaka; Masashi Hashimoto, all of Tsukuba, Japan

[73] Assignee: Fujisawa Pharmaceutical Co., Ltd., Osaka, Japan

[21] Appl. No.: 187,240

[22] Filed: Apr. 28, 1988

[30] Foreign Application Priority Data

May 1, 1987 [GB] United Kingdom ............... 8710352
Jul. 13, 1987 [GB] United Kingdom ............... 8716438
Dec. 23, 1987 [GB] United Kingdom ............... 8730027

[51] Int. Cl.$^4$ ............... A61K 31/40; C07D 207/10; C07F 9/02
[52] U.S. Cl. ............... 514/426; 548/557; 548/413; 514/91
[58] Field of Search ............... 548/557, 413; 514/426, 514/91

[56] References Cited

U.S. PATENT DOCUMENTS 4,210,660  7/1980  Takashima et al. ............... 548/557
4,785,119 11/1988  Hojo et al. ............... 548/557

FOREIGN PATENT DOCUMENTS 61-257966 11/1986  Japan ............... 548/557
63-51370   3/1988  Japan ............... 548/557

OTHER PUBLICATIONS

Frans M. Kaspersen et al.: J.C.S. Perkin I 1975, pp. 1617–1622.
Frans M. Kaspersen et al.: J.C.S. Perkin I 1975, pp. 1798–1802.
Patrick E. Hanna et al.: Journal of Medical Chemistry, 1973, vol. 16, No. 9, pp. 963–967.
A. M. Sepulchre et al.: Carbohyd. Res., 14 (1970) 1–8.
A. M. Sepulchre et al.: C. R. Acad. Sc. Paris, t. 268 (3 March, 1969), pp. 849–851.
Frans M. Kaspersen et al.: Heterocycles 2 (1974), pp. 15–19.

*Primary Examiner*—Mary C. Lee
*Assistant Examiner*—Robert C. Whittenbaugh

*Attorney, Agent, or Firm*—Oblon, Spivak, McClelland, Maier & Neustadt

[57] ABSTRACT

The invention relates to novel compounds of the formula:

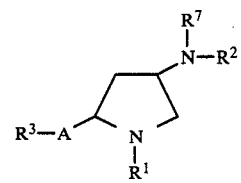

wherein $R^1$ is hydrogen, lower alkoxycarbonyl, phenylsulfonyl, phenylsulfonyl substituted with 1 to 3 substituent(s) selected from the group consisting of halogen, nitro, lower alkoxy, mono (or di or tri)halo(lower)alkyl and lower alkyl, phenylcarbamoyl, lower alkylsulfonyl, benzoyl or thienylsulfonyl;

$R^2$ is phenylsulfonyl or phenylsulfonyl substituted with 1 to 3 substituent(s) selected from the group consisting of halogen, lower alkyl, lower alkoxy and mono(or di or tri)halo(lower)alkyl, $R^3$ is carboxy(lower)alkyl, lower alkyl substituted with carboxy and 1 to 3 halogen atom(s), esterified carboxy(lower)alkyl, carbamoyl(lower)alkyl, lower alkylsulfonylcarbamoyl(lower)alkyl, phenylsulfonylcarbamoyl(lower)alkyl, carboxyphenyl, esterified carboxyphenyl, carboxy, esterified carboxy, hydroxy(lower)alkyl, sulfino(lower)alkyl, phosphono(lower)alkyl, di(lower)alkoxyphosphoryl(lower)alkyl or halo(lower)alkyl, $R^7$ is hydrogen or lower alkyl, and A is

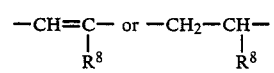

in which $R^8$ is hydrogen or lower alkyl, or a pharmaceutically acceptable salt thereof, useful as therapeutic agents for thrombosis, asthma and nephritis.

9 Claims, No Drawings

PYRROLIDINE DERIVATIVES AS ANTIASTHMATICS

This invention relates to new pyrrolidine derivatives and pharmaceutically acceptable salts thereof.

More particularly, it relates to new pyrrolidine derivatives and pharmaceutically acceptable salts thereof which are thromboxane $A_2$ ($TXA_2$) antagonists and therefore useful as therapeutical agents for diseases such as thrombosis, asthma, nephritis or the like.

The pyrrolidine derivatives of this invention can be represented by the following formula (I):

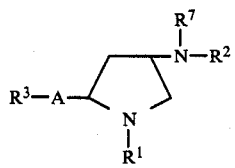

(I)

wherein
R$^1$ is hydrogen or an acyl group,
R$^2$ is an acyl group,
R$^3$ is carboxy(lower)alkyl, lower alkyl substituted with carboxy and one or more halogen atom(s), protected carboxy(lower)alkyl, carboxyaryl, protected carboxyaryl, carboxy, protected carboxy hydroxy(lower)alkyl, sulfino(lower)alkyl, phosphono(lower)alkyl, protected phosphono(lower)alkyl or halo(lower)alkyl,
R$^7$ is hydrogen or lower alkyl, and
A is

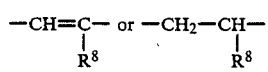

(in which R$^8$ is hydrogen or lower alkyl).

According to the present invention, the new pyrrolidine derivatives (I) can be prepared by the processes which are illustrated in the following scheme.

Process 1

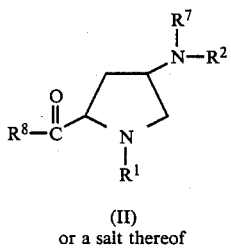 +  ⟶

(II)
or a salt thereof (III)
or a salt thereof

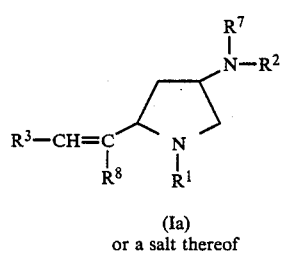

(Ia)
or a salt thereof

Process 2

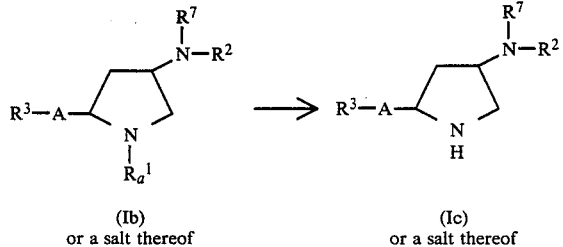

(Ib)
or a salt thereof (Ic)
or a salt thereof

Process 3

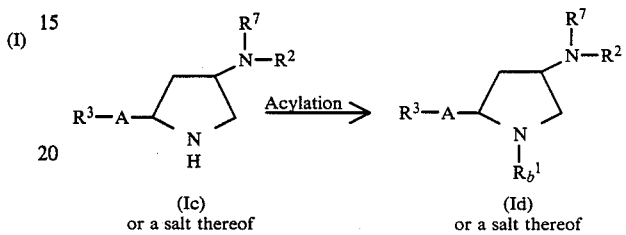

(Ic)
or a salt thereof (Id)
or a salt thereof

Process 4

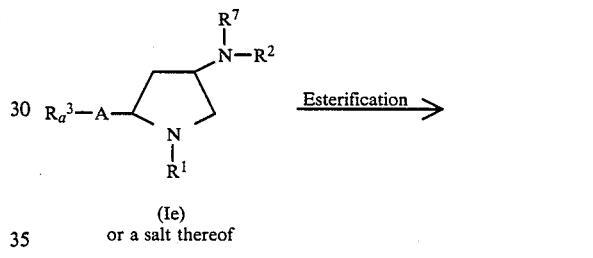

(Ie)
or a salt thereof

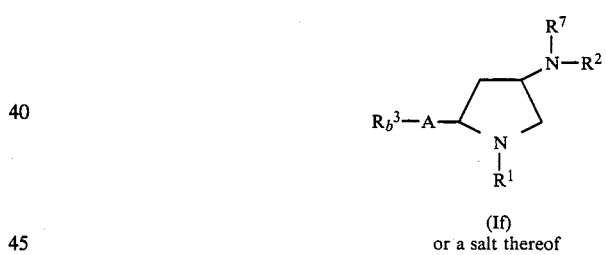

(If)
or a salt thereof

Process 5

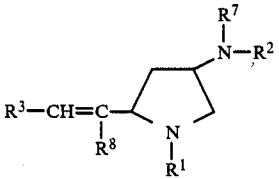

(Ia)
or a salt thereof

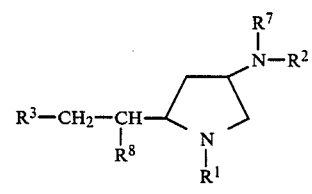

(Ig)
or a salt thereof

Process 6
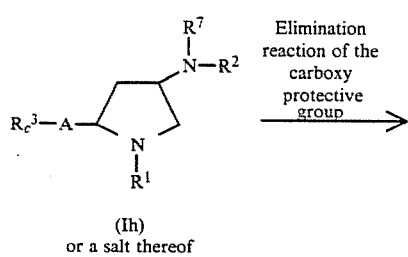
(Ih)
or a salt thereof
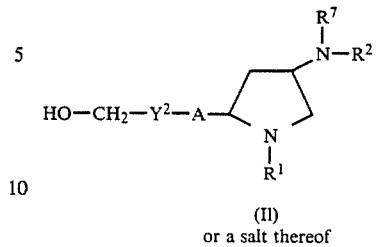
(Il)
or a salt thereof
Process 9
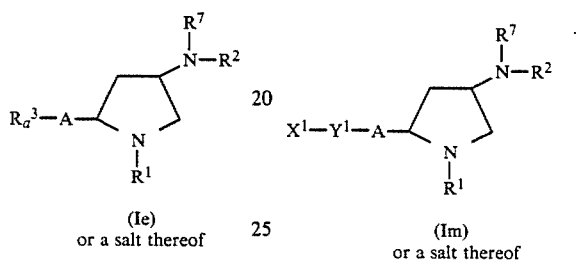
Process 7
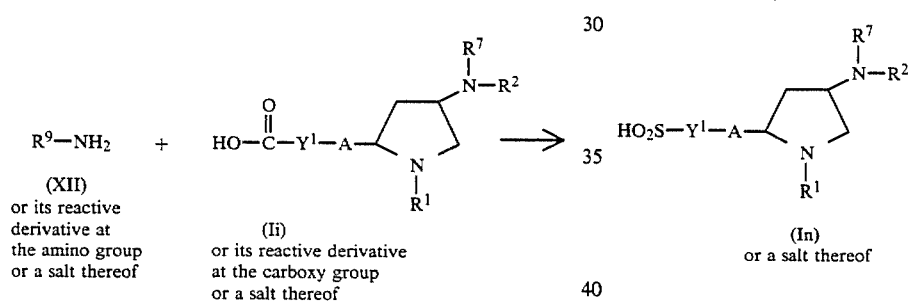
Process 10
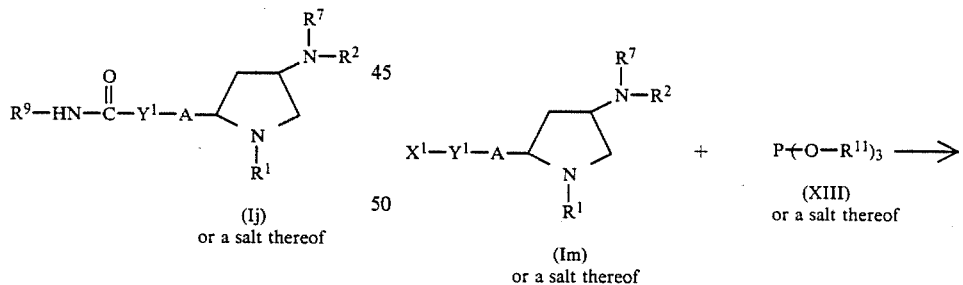
Process 8
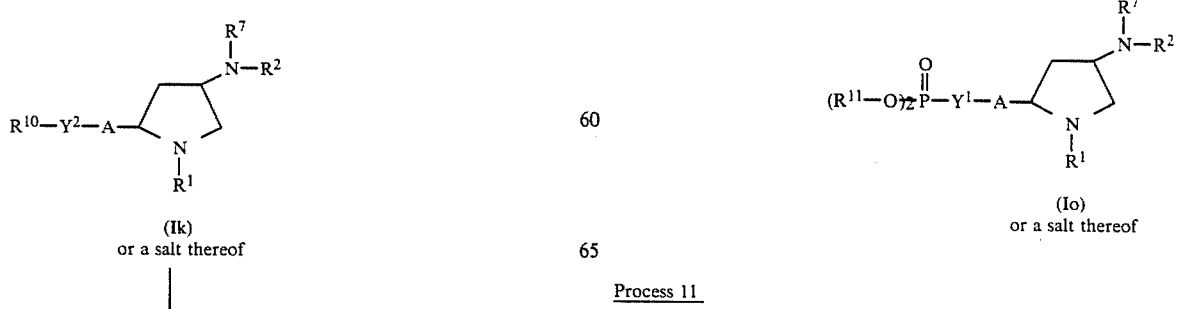
Process 11

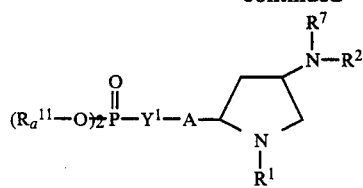

(Ip)
or a salt thereof

Elimination reaction of the phosphono protective group

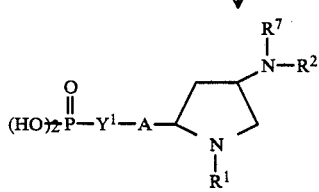

(Iq)
or a salt thereof

Process 12

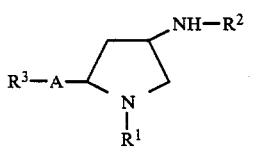 + $R_a^7-X^2$ ⟶
(Ir)      (XIV)
or a salt thereof

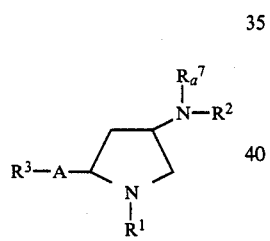

(Is)
or a salt thereof wherein
$R^1$, $R^2$, $R^3$, $R^7$, A and $R^8$ are each as defined above,
$R^4$ is aryl,
$R_a^1$ is an amino protective group,
$R_b^1$ is an acyl group,
$R_a^3$ is carboxy(lower)alkyl, carboxyaryl or carboxy,
$R_b^3$ is esterified carboxy(lower)alkyl, esterified carboxyaryl or esterified carboxy,
$R_c^3$ is protected carboxy(lower)alkyl, protected carboxyaryl or protected carboxy,
$R^9$ is hydrogen, lower alkylsulfonyl or arylsulfonyl,
$Y^1$ is lower alkylene,
$R^{10}$ is protected carboxy,
$Y^2$ is $C_1-C_5$ alkylene,
$X^1$ is halogen,
$R^{11}$ is hydrogen or a phosphono protective group,
$R_a^{11}$ is a phosphono protective group,
$R_a^7$ is lower alkyl, and
$X^2$ is halogen.

The starting compound (II) is novel and can be prepared by the following processes.

Process A

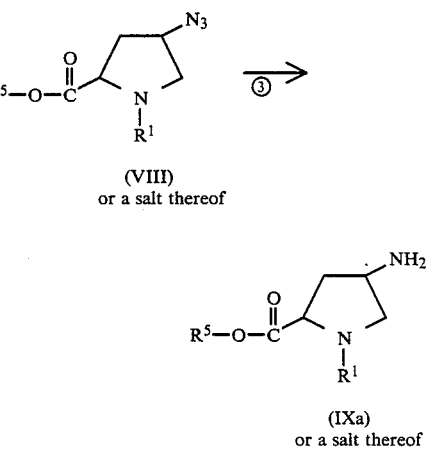

(IV)
or a salt thereof $\xrightarrow{X^3-SO_2-R^6 \text{ (V)}}{①}$

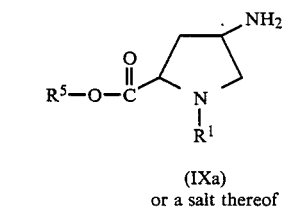

(VI)
or a salt thereof $\xrightarrow{MN_3 \text{ (VII)}}{②}$

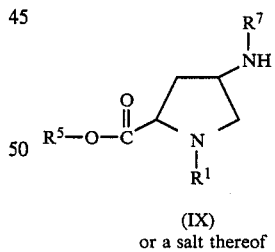

(VIII)
or a salt thereof

③ ⟶

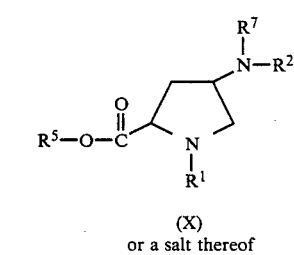

(IXa)
or a salt thereof

Process B

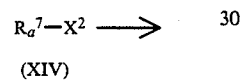

(IX)
or a salt thereof acylation ⟶

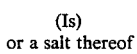

(X)
or a salt thereof

Process C

-continued

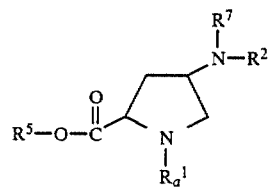

(Xa) or a salt thereof

① ↓

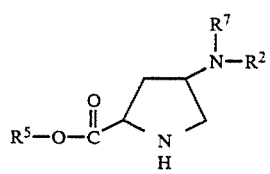

(Xb) or a salt thereof

② ↓

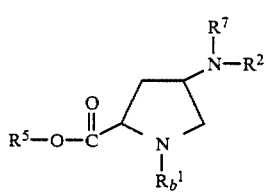

(Xc) or a salt thereof

Process D

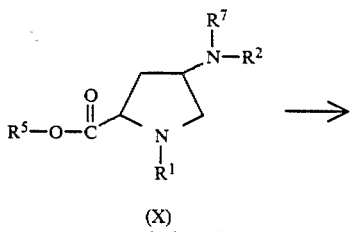

(X) or a salt thereof

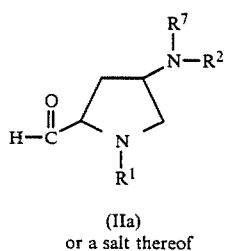

(IIa) or a salt thereof

Process E

-continued

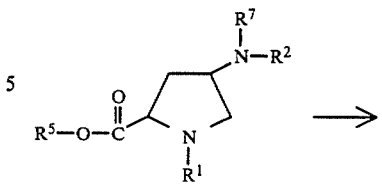

(X) or a salt thereof

→

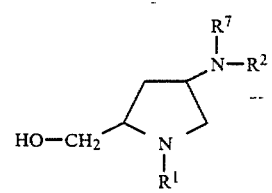

(XIa) or a salt thereof

Process F

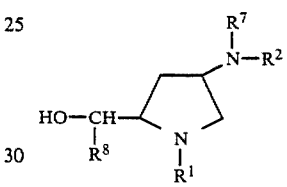

(XI) or a salt thereof

↓

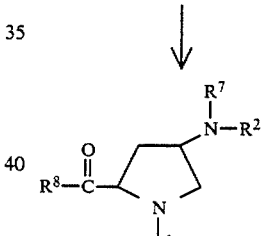

(II) or a salt thereof wherein
$R^1$, $R_a^1$, $R_b^1$, $R^2$, $R^7$ and $R^8$ are each as defined above,
$R^5$ is lower alkyl,
$R^6$ is lower alkyl,
$X^3$ is halogen, and
M is an alkaline metal.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, lysine and the like.

Suitable salts of the compounds(Ia)–(Is), (II), (IIa), (IV), (VI), (VIII), (IX), (IXa), (X), (Xa), (Xb), (Xc), (XI) and (XIa) are the same as those exemplified in the explanation of pharmaceutically acceptable salt of the compound (I).

Suitable salts of the compounds (III) and (XIII) are the same base salt as those exemplified in the explanation of the compound (I).

Suitable salts of the compound (XII) are the same acid salt as those exemplified in the explanation of the compound (I).

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "acyl" may include lower alkanoyl (e.g., formyl, acetyl, propionyl, butyryl, isobutyryl, valeryl, isovaleryl, pivaloyl, etc.), lower alkoxycarbonyl (e.g., methoxycarbonyl, ethoxycarbonyl, propoxycarbonyl, isopropoxycarbonyl, butoxycarbonyl, t-butoxycarbonyl, pentyloxycarbonyl, t-pentyloxycarbonyl, hexyloxycarbonyl, etc.), lower alkylsulfonyl (e.g. methylsulfonyl, ethylsulfonyl, propylsulfonyl, isopropylsulfonyl, butylsulfonyl, t-butylsulfonyl, pentylsulfonyl, t-pentylsulfonyl, hexylsulfonyl, etc.), arylsulfonyl (e.g., phenylsulfonyl, naphtylsulfonyl, etc.), aroyl (e.g. benzoyl, naphthoyl, etc.), ar(lower)alkanoyl (e.g., phenylacetyl, phenylpropionyl, etc.), cyclo(lower)alkyl(lower)alkanoyl (e.g. cyclohexylacetyl, cyclopentylacetyl, etc.), ar(lower)alkoxycarbonyl (e.g., benzyloxycarbonyl, phenethyloxycarbonyl, etc.), arylcarbamoyl (e.g., phenylcarbamoyl, naphtylcarbamoyl, etc.), heterocyclicsulfonyl such as heteromonocyclicsulfonyl (e.g., thienylsulfonyl, furylsulfonyl, pyridylsulfonyl, etc.) and the like; and said acyl groups may be substituted with 1 to 3 suitable substituent(s) such as halogen (e.g., chlorine, bromine, fluorine and iodine), lower alkyl (e.g., methyl, ethyl, propyl, isopropyl, butyl, isobutyl, sec-butyl, t-butyl, pentyl, t-pentyl, hexyl, etc.), lower alkoxy (e.g. methoxy, ethoxy, propoxy, isopropoxy, butoxy, t-butoxy, pentyloxy, t-pentyloxy, hexyloxy, etc.), nitro, mono(or di or tri)halo(lower)alkyl (e.g. chloromethyl, bromomethyl, chloropropyl, 1,2-dichloroethyl, 1,2-dibromoethyl, 2,2-dichloroethyl, trifluoromethyl, 1,2,2-trichloroethyl, etc.) or the like.

Suitable "lower alkyl" and "lower alkyl moiety" in the terms "carboxy(lower)alkyl", "protected carboxy(lower)alkyl", "esterified carboxy(lower)alkyl", "hydroxy(lower)alkyl", "sulfino(lower)alkyl", "phosphono(lower)alkyl", "protected phosphono(lower)alkyl", "halo(lower)alkyl" and "lower alkylsulfonyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like.

Suitable "protected carboxy" and "protected carbox moiety" in the terms "protected carboxy(lower)alkyl" and "protected carboxyaryl" may include carbamoyl; acylcarbamoyl such as lower alkylsulfonylcarbamoyl (e.g., methylsulfonylcarbamoyl, ethylsulfonylcarbamoyl, propylsulfonylcarbamoyl, isopropylsulfonylcarbamoyl, butylsulfonylcarbamoyl, t-butylsulfonylcarbamoyl, pentylsulfonylcarbamoyl, t-pentylsulfonylcarbamoyl, hexylsulfonylcarbamoyl, etc.), arylsulfonylcarbamoyl (e.g., phenylsulfonylcarbamoyl, naphtylsulfonylcarbamoyl, etc.) or the like; esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.), lower alkenyl ester (e.g., vinyl ester, allyl ester, etc.), lower alkynyl ester (e.g. ethynyl ester, propynyl ester, etc.), mono(or di or tri)-halo(lower)alkyl ester (e.g., 2-iodoethyl ester, 2,2,2-trichloroethyl ester, etc.), lower alkanoyloxy(lower)alkyl ester (e.g., acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.), lower alkanesulfonyl(lower)alkyl ester (e.g., mesylmethyl ester, 2-mesylethyl ester, etc.), ar(lower)alkyl ester, for example, phenyl(lower)alkyl ester which may be substituted with one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.), lower alkoxycarbonyloxy(lower)alkyl ester (e.g., methoxycarbonyloxymethyl ester, ethoxycarbonyloxymethyl ester, ethoxycarbonyloxyethyl ester, etc.), aroyloxy(lower)alkyl ester (e.g., benzoyloxymethyl ester, benzoyloxyethyl ester, toluoyloxyethyl ester, etc.), aryl ester which may have one or more suitable substituent(s) (e.g., phenyl ester, tolyl ester, tertiarybutylphenyl ester, xylyl ester, mesityl ester, cumenyl ester, etc.); and the like.

Suitable "aryl" and "aryl moiety" in the terms "carboxyaryl", "esterified carboxyaryl", "protected carboxyaryl" and "arylsulfonyl" may include phenyl, naphtyl and the like.

Suitable "protected phosphono moiety" in the term "protected phosphono(lower)alkyl" may include di(lower)alkoxyphosphoryl (e.g., dimethoxyphosphoryl, diethoxyphosphoryl, dipropoxyphosphoryl, etc.), and the like.

Suitable "halogen" may include chlorine, bromine, fluorine and iodine.

Suitable "amino protective group" may include an acyl group as mentioned above and the like.

Suitable "esterified carboxy" and "esterified carboxy moiety" in the terms "esterified carboxy(lower)alkyl" and "esterified carboxyaryl" can be referred to the ones as exemplified above.

Suitable lower alkylene may include straight or branched one having 1 to 6 carbon atoms, such as methylene, ethylene, trimethylene, propylene, tetramethylene, ethylethylene, tetramethylene, pentamethylene, hexamethylene or the like.

Suitable phosphono protective group may include lower alkyl as mentioned above, and the like.

Suitable "alkaline metal" may include sodium, potassium and the like.

Preferred embodiments of the object compound (I) are as follows.

Preferred embodiment of $R^1$ is hydrogen, lower alkoxycarbonyl, phenylsulfonyl, phenylsulfonyl substituted with 1 to 3 substituent(s) selected from the group consisting of halogen, nitro, lower alkoxy, mono(or di or tri)halo(lower)alkyl and lower alkyl, phenylcarbamoyl, lower alkylsulfonyl, benzoyl or thienylsulfonyl;

$R^2$ is phenylsulfonyl or phenylsulfonyl substituted with 1 to 3 substituent(s) selected from the group consisting of halogen, lower alkyl, lower alkoxy and mono (or di or tri)halo(lower)alkyl, R³ is carboxy(lower)alkyl, protected carboxy(lower)alkyl [more preferably esterified carboxy(lower)alkyl, carbamoyl(lower)alkyl or acylcarbamoyl(lower)alkyl, most preferably lower alkoxycarbonyl(lower)alkyl, carbamoyl(lower)alkyl, lower alkylsulfonylcarbamoyl(lower)alkyl or phenylsulfonylcarbamoyl(lower)alkyl], carboxy phenyl, protected carboxy phenyl [more preferably esterified carboxyphenyl, most preferably lower alkoxycarbonylphenyl], carboxy, protected carboxy [more preferably esterified carboxy, most preferably lower alkoxycarbonyl], hydroxy(lower)alkyl, sulfino(lower)alkyl, phosphono(lower)alkyl, protected phosphono(lower)alkyl [more preferably di(lower)alkoxyphosphoryl(lower)alkyl], halo(lower)alkyl, or lower alkyl substituted with carboxy and 1 to 3 halogen atom(s);

R⁷ is hydrogen or lower alkyl; and

A is

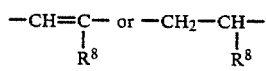

(in which R⁸ is hydrogen or lower alkyl). The processes for preparing the object compound (I) and starting compound (II) of the present invention are explained in detail in the following.

Process 1

The compound (Ia) or a salt thereof can be prepared by reacting the compound (II) or a salt thereof with the compound (III) or a salt thereof.

The reaction is usually carried out in a conventional solvent such as acetone, dioxane, acetonitrile, chloroform, methylene chloride, ethylene chloride, tetrahydrofuran, ethyl acetate, N,N-dimethylformamide, dimethyl sulfoxide or any other solvent which does not adversely influence the reaction.

The reaction temperature is not critical and the reaction is usually carried out under cooling to heating.

Process 2

The compound (Ic) or a salt thereof can be prepared by subjecting the compound (Ib) or a salt thereof to elimination reaction of the imino protective group.

The present elimination reaction is carried out in accordance with a conventional method such as hydrolysis; reduction; or the like. The hydrolysis may include a method using an acid or base and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of the protective group to be eliminated. When the elimination reaction is conducted with the acid, it can be carried out in the presence or absence of a solvent. Suitable solvent may include a conventional organic solvent (e.g., methanol, ethanol, tetrahydrofuran, etc.), water or a mixture thereof.

The hydrolysis with a base is preferably applied for eliminating acyl group, for example, haloalkanoyl (e.g. dichloroacetyl, trifluoroacetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, cesium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.) or the like. The hydrolysis using a base is often carried out in water, a conventional organic solvent or a mixture thereof. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.) or the like. Suitable reduction may include, for example, reduction with an alkali metal borohydride (e.g. sodium borohydride, etc.) and the like.

The reaction temperature is not critical and may be suitably selected in accordance with the kind of the imino protective group and the elimination method as mentioned above, and the present reaction is preferably carried out under a mild condition such as under cooling, at ambient temperature or slightly elevated temperature.

Process 3

The compound (Id) or a salt thereof can be prepared by reacting the compound (Ic) or a salt thereof with an acylating agent.

The acylating agent may include an organic acid (i.e. $R_b^1$-OH in which $R_b^1$ is acyl) or its reactive derivative or a salt thereof.

The suitable reactive derivative of the organic acid may be a conventional one such as an acid halide (e.g. acid chloride, acid bromide, etc.), an acid azide, an acid anhydride, an activated amide, an activated ester, an isocyanate [e.g. aryl isocyanate (e.g. phenyl isocyanate, etc.), etc.].

When free acid is used as an acylating agent, the acylation reaction may preferably be conducted in the presence of a conventional condensing agent such as N,N'-dicyclohexylcarbodiimide or the like.

The reaction can preferably be conducted in the presence of an inorganic or organic base as exemplified in the explanation of the above Process 2.

This reaction is usually carried out in a solvent which does not adversely influence the reaction such as methanol, ethanol, propanol, dichloromethane, tetrahydrofuran, chloroform and the like.

The reaction temperature is not critical and the reaction can be carried out under cooling to under heating.

Process 4

The compound (If) or a salt thereof can be prepared by subjecting the compound (Ie) or a salt thereof to esterification reaction. The esterifying agent to be used in this reaction may include a conventional one such as an alcohol or its reactive equivalent (e.g. halide, sulfonate, sulfate, diazo compound, etc.) or the like.

The reaction is usually carried out in a conventional solvent such as acetone, dioxane, alcohol, chloroform, methylene chloride, ethylene chloride, tetrahydrofuran, ethyl acetate, N,N-dimethylformamide, dimethyl sulfoxide or any other solvent which does not adversely influence the reaction.

The reaction temperature is not critical and the reaction is usually carried out under cooling to warming.

Process 5

The compound (Ig) or a salt thereof can be prepared by subjecting the compound (Ia) or a salt thereof to reduction.

The reduction method applicable for the present reaction may include catalytic reduction.

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reaction is usually carried out in a conventional solvent such as acetone, dioxane, alcohol, tetrahydrofuran, ethyl acetate, N,N-dimethylformamide, dimethyl sulfoxide or any other solvent which does not adversely influence the reaction.

The reaction temperature is not critical and the reaction is usually carried out under cooling to heating.

Process 6

The compound (Ie) or a salt thereof can be prepared by subjecting the compound (Ih) or a salt thereof to elimination reaction of the carboxy protective group.

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), or the like.

Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.).

Reduction can be applied preferably for elimination of the protective group such as 4-nitrobenzyl, 2-iodoethyl, 2,2,2-trichloroethyl, or the like. The reduction method applicable for the elimination reaction may include, for example reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The reaction is usually carried out in a solvent such as water, an alcohol (e.g. methanol, ethanol, etc.), or any other solvent which does not adversely influence the reaction. A liquid base or acid can be also used as the solvent. The reaction temperature is not critical and the reaction is usually carried out under cooling to warming.

Process 7

The compound (Ij) or a salt thereof can be prepared by reacting the compound (XII) or its reactive derivative at the amino group or a salt thereof with the compound (Ii) or its reactive derivative at the carboxy group or a salt thereof.

Suitable reactive derivative at the carboxy group of the compound (Ii) may include an acid halide (e.g. acid chloride, acid bromide, etc.), an acid azide, an acid anhydride, an activated amide, an activated ester and the like.

In this reaction, when the compound (Ii) is used in a free acid form or its salt form, the reaction is preferably carried out in the presence of a conventional condensing agent such as N,N'-dicyclohexylcarbodiimide or the like.

The reaction can preferably be conducted in the presence of an inorganic or organic base as exemplified in the explanation of the above Process 2.

The reaction is usually carried out in a conventional solvent such as acetone, dioxane, chloroform, methylene chloride, ethylene chloride, tetrahydrofuran, N,N-dimethylformamide, dimethyl sulfoxide or any other solvent which does not adversely influence the reaction.

The reaction temperature is not critical and the reaction is usually carried out under cooling to heating.

Process 8

The compound (Il) or a salt thereof can be prepared by reducing the compound (Ik) or a salt thereof.

The reduction is usually carried out by using a reducing agent such as di(lower)alkylalminum hydride (e.g., diisobutylalminum hydride, etc.), alkali metal alminum hydride (e.g., lithium alminum hydride, sodium alminum hydride, potassium alminum hydride, etc.) or the like.

The reaction is usually carried out in a conventional solvent such as toluene, tetrahydrofuran, or any other solvent which does not adversely influence the reaction.

The reaction temperature is not critical and the reaction is usually carried out under cooling or ambient temperature.

Process 9

The compound (In) or a salt thereof can be prepared by reacting the compound (Im) or a salt thereof with sulfite.

Suitable sulfite may include alkali metal sulfite (e.g., sodium sulfite, etc.) and the like.

The reaction is usually carried out in a conventional solvent such as water, dimethyl sulfoxide, N,N-dimethylformamide or any other solvent which does not adversely influence the reaction.

The reaction temperature is not critical and the reaction is usually carried out under warming to heating.

Process 10

The compound (Io) or a salt thereof can be prepared by reacting the compound (Im) or a salt thereof with the compound (XIII) or a salt thereof.

The reaction is usually carried out in the presence or absence of a conventional solvent.

The reaction temperature is not critical and the reaction is usually carried out under warming to heating.

Process 11

The compound (Iq) or a salt thereof can be prepared by subjecting the compound (Ip) or a salt thereof to elimination reaction of the phosphono protective group. This reaction can be carried out in accordance with a conventional method such as a method by treating the compound (Ip) with halo-tri(lower)alkyl-silane (e.g., bromotrimethylsilane, iodotrimethylsilane, etc.) or the like.

The reaction is usually carried out in a conventional solvent such as dihaloalkane (e.g., dichloromethane, dichloroethane, etc.), chloroform, tetrahydrofuran, or any other solvent which does not adversely influence the reaction.

The reaction temperature is not critical and the reaction is usually carried out under cooling to warming.

Process 12

The compound (Is) or a salt thereof can be prepared by reacting the compound (Ir) or a salt thereof with the compound (XIV).

The reaction is usually carried out in the presence or absence of a conventional solvent.

The reaction temperature is not critical and the reaction is usually carried out under cooling to warming.

Process A- ①

The compound (VI) or a salt thereof can be prepare by reacting the compound (IV) or a salt thereof with the compound (V).

The reaction is usually carried out in a conventional solvent such as dichloromethane, or any other solvent which does not adversely influence the reaction.

The reaction is preferably carried out in the presence of inorganic or organic base as exemplified in the explanation of the above Process 2.

Process A- ②

The compound (VIII) or a salt thereof can be prepared by reacting the compound (VI) or a salt thereof with the compound (VII).

The reaction is usually carried out in a conventional solvent such as dimethyl sulfoxide or any other solvent which does not adversely influence the reaction.

The reaction temperature is not critical and the reaction is usually carried out under warming to heating.

Process A- ③

The compound (IXa) or a salt thereof can be prepared by subjecting the compound (VIII) or a salt thereof to hydrogenation. This reaction is usually carried out in the presence of catalysts such as palladium on carbon or the like.

The reaction is usually carried out in a conventional solvent such as alcohol (e.g., methanol, ethanol, etc.), or any other solvent which does not adversely influence the reaction.

The reaction temperature is not critical and the reaction is usually carried out under cooling to heating.

Process B

The compound (X) or a salt thereof can be prepared by reacting the compound (IX) or a salt thereof with an acylating agent. The acylating agent may include an organic acid (i.e. $R^2$-OH in which $R^2$ is acyl) or its reactive derivative or a salt thereof.

The suitable reactive derivative of the organic acid may be a conventional one such as an acid halide (e.g. acid chloride, acid bromide, etc.), an acid azide, an acid anhydride, an activated amide, an activated ester, an isocyanate [e.g. aryl isocyanate (e.g. phenyl isocyanate, etc.), etc.].

When free acid is used as an acylating agent, the acylation reaction may preferably be conducted in the presence of a conventional condensing agent such as N,N'-dicyclohexylcarbodiimide and the like.

The reaction can preferably be conducted in the presence of an inorganic or organic base as exemplified in the explanation of the above Process 2.

This reaction is usually carried out in a solvent which does not adversely influence the reaction such as methanol, ethanol, propanol, dichloromethane, tetrahydrofuran, chloroform and the like.

The reaction temperature is not critical and the reaction is usually carried out under cooling to under heating.

Process C- ①

The compound (Xb) or a salt thereof can be prepared by subjecting the compound (Xa) or a salt thereof to elimination reaction of the imino protective group.

This reaction is carried out by substantially the same method as that of Process 2, and therefore the reaction conditions (e.g., reaction temperature, solvent, etc.) are to be referred to said Process 2.

Process C- ②

The compound (Xc) or a salt thereof can be prepared by reacting the compound (Xb) or a salt thereof with an acylating agent.

This reaction is carried out by substantially the same method as that of Process 3, and therefore the reaction conditions (e.g., reaction temperature, solvent, acylating agent, etc.) are to be referred to said Process 3.

Process D

The compound (IIa) or a salt thereof can be prepared by reducing the compound (X) or a salt thereof.

This reaction is carried out by substantially the same method as that of Process 8, and therefore the reaction conditions (e.g., reaction temperature, solvent, reducing agent, etc.) are to be referred to said Process 8.

Process E

The compound (XIa) or a salt thereof can be prepared by reducing the compound (X) or a salt thereof.

This reaction is carried out by substantially the same method as that of Process 8, and therefore the reaction conditions (e.g., reaction temperature, solvent, reducing agent, etc.) are to be referred to said Process 8.

Process F

The compound (II) or a salt thereof can be prepared by oxidizing the compound (XI) or a salt thereof.

The oxidation is carried out by using a conventional oxidizing agent (e.g. chromium trioxide, dimethyl sulfoxide, etc.)

The reaction is usually carried out in a conventional solvent such as chloroform, tetrahydrofuran, dihaloalkane (e.g., dichloromethane, dichloroethane, etc.), dimethyl sulfoxide, or anyl other solvent which does not adversely influence the reaction.

The reaction temperature is not critical and the reaction is usually carried out under cooling or ambient temperature.

The object compound (I) of this invention and pharmaceutically acceptable salts thereof are thromboxane $A_2(TXA_2)$ antagonists and therefore useful as therapeutic agents for diseases such as thrombosis, asthma, nephritis or the like.

For illustration purpose, some biological data of the object compound (I) are shown in the followings.

In the following tests, the used 9, 11-azo $PGH_2$ and 9,11-methanoepoxy $PGH_2$(U46619) are characterized pharmacologically as $TXA_2$ mimetic agents and widely used for evaluating $TXA_2$ antagonism of test compounds (for example, vide The Journal of Pharmacology and Experimental Therapeutics Vol. 234, pp 435-441).

Test compound (1) Sodium salt of (2S,4R)-2-[(E and Z)-5-carboxy-1-pentenyl]-1-(4-chlorophenylsulfonyl)-4-(4-chlorophenylsulfonylamino)pyrrolidine.

(2) (2S,4R)-2-[(Z)-5-Carboxy-1-pentenyl]-1-(4-chlorophenylsulfonyl)-4-(4-chlorophenylsulfonylamino)pyrrolidine Test 1 (Effect on 9,11-azo $PGH_2$ induced aggregation of rabbit platelet in vitro) (a) Test method In the in vitro experiments, the blood was collected from the carotid artery of rabbits into plastic vessels containing 0.1 volume of 3.8% aqueous sodium citrate. Platelet rich plasma (PRP) was prepared by centrifugation at 150 g for 15 minutes. Platelet aggregation was investigated using the turbidometric method with an aggregometer (NKK HEMATRACER 1). To the 225 μl of PRP, 25 μl of test compound solution was added, and then stirred at 1000 rpm for 2 minutes at 37° C. To the solution, 5 μl of 9,11-azo $PGH_2$ (final 1.0 μM) was added as an aggregating inducer. $IC_{50}$ (Inhibition concentration of platelet aggregation by 50%) were graphically determined.

(b) Test result

| Test compounds | $IC_{50}$ (M) |
|---|---|
| (1) | $8.5 \times 10^{-8}$ |
| (2) | $5.5 \times 10^{-8}$ |

Test 2. (Effect on 9,11-methanoepoxy $PGH_2$ induced platelet aggregation ex vivo)
(a) Test method In the ex vivo experiments, male Hartley strain guinea-pigs weighing about 300 g were used after overnight fasting. Animals received an oral administration of test compound (0.032 mg/kg) or vehicle 1 hour before the blood collection from abdominal artery PRP was prepared as described above, and platelet aggregation was induced by adding 5 μl of 9,11-methanoepoxy $PGH_2$ (U46619, 0.5 μM) to 250 μl of PRP.

(b) Test result

| Test compounds | Inhibition (%) |
|---|---|
| (1) | 94.2 |
| (2) | 100 |

The object compound (I) or its pharmaceutically acceptable salts can usually be administered to mammals including human being in the form of a conventional pharmaceutical composition such as capsule, micro-capsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petroleum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

(1) To a solution of (2S,4R)-1-t-butoxycarbonyl-4-hydroxy-2-methoxycarbonylpyrrolidine (53.4 g) in dichloromethane (500 ml) were added triethylamine (36 ml) and methanesulfonyl chloride (19.8 ml) under ice bath cooling and the mixture was stirred at the same temperature for 3 hours. The solution was washed successively with diluted hydrochloric acid, saturated aqueous sodium bicarbonate and brine and dried over magnesium sulfate. The solvent was evaporated in vacuo and the residue was crystallized from n-hexane to give (2S,4R)-1-t-butoxycarbonyl-4-methylsulfonyloxy- 2-methoxycarbonylpyrrolidine (56.2 g) as colorless crystal.

mp: 73°–75° C.

$^1$H-NMR (CDCl$_3$) δppm: 1.43 (9H ×2/3, s), 1.47 (9H×1/3, , s), 2.28 (1H, ddd, J=5, 8, 14 Hz), 2.63 (1H, m), 3.05 (3H, s), 3.7–3.9 (2H, m), 3.77 (3H, s), 4.41 (2/3H, t, J=8 Hz), 4.48 (1/3H, t, J=8 Hz), 5.28 (1H, m)

The following compounds were obtained according to a similar manner to that of Preparation 1(1).

(2) (2R,4R)-4-Methylsulfonyloxy-2-methoxycarbonyl-1-phenylsulfonylpyrrolidine $^1$H-NMR (CDCl$_3$) δppm: 2.32 (ddd, J=4.5, 9, 13.5 Hz, 1H), 2.58 (m, 1H), 2.84 (s, 3H), 3.79 (s, 3H), 3.7–3.8 (m, 2H), 4.46 (t, J=12 Hz, 1H), 5.23 (m, 1H), 7.5–7.7 (m, 3H), 7.9–8.0 (m, 2H)

(3) (2R,4S)-4-Methylsulfonyloxy-2-methoxycarbonyl-1-phenylsulfonylpyrrolidine $^1$H-NMR (CDCl$_3$) δppm: 2.30 (ddd, J=4.5, 9, 13.5 Hz, 1H), 2.58 (m, 1H), 3.82 (s, 3H), 3.7–3.9 (m, 2H), 3.77 (s, 3H), 4.45 (t, J=8 Hz, 1H), 5.23 (m, 1H), 7.5–7.7 (m, 3H), 7.9–8.0 (m, 2H)

Preparation 2

To a solution of (2S,4S)-1-t-butoxycarbonyl-4-hydroxy-2-methoxycarbonylpyrrolidine (20.0 g) in dichloromethane (500 ml) were added triethylamine (13.5 ml) and methanesulfonyl chloride (7.4 ml) with stirring in an ice bath and the mixture was stirred at the same temperature for 4 hours. The solution was washed successively with diluted hydrochloric acid, saturated aqueous sodium bicarbonate and brine and dried over magnesium sulfate. The solvent was evaporated in vacuo to give (2S,4S)-1-t-butoxycarbonyl-4-methylsulfonyloxy-2-methoxycarbonylpyrrolidine (27.7 g) as a pale brown oil.

$^1$H-NMR (CDCl$_3$) δppm: 1.43 (s, 9×3/5H), 1.46 (s, 9×2/5H), 2.53 (m, 2H), 3.03 (s, 3H), 3.76 (s, 3H), 3.80 (m, 2H), 4.4–4.6 (m, 1H), 5.75 (m, 1H)

Preparation 3

(1) A mixture of (2S,4R)-1-t-butoxycarbonyl-4-methylsulfonyloxy-2-methoxycarbonylpyrrolidine (32.3 g) and sodium benzoate (28.8 g) in dimethyl sulfoxide (320 ml) was stirred at 90° C. overnight and cooled to room temperature. The mixture was diluted with ethyl acetate (600 ml) and washed successively with water and brine. The organic phase was dried over magnesium sulfate and the solvent was evaporated in vacuo to give an oil. The oil was crystallized from n-hexane to give (2S,4S)-4-benzoyloxy-1-t-butoxycarbonyl-2-methoxycarbonylpyrrolidine (31.0 g) as a colorless crystal.

mp: 89°–90° C.

$^1$H-NMR (CDCl$_3$) δppm: 1.45 (s, 9/2H), 1.48 (s, 9/2H), 2.4–2.7 (m, 2H), 3.68 (s, 3/2H), 3.69 (s, 3/2H), 3.69 (m, 1H), 3.82 (m, 1H), 4.48 (dd, J=2, 11 Hz, 1/2H), 4.61 (dd, J=4, 11 Hz, 1/2H), 5.53 (m, 1H), 7.43 (t, J=7.5 Hz, 1H), 7.57 (t, J=7.5 Hz, 2H), 7.98 (d, J=7.5 Hz, 2H)

The following compound was obtained according to a similar manner to that of Preparation 3(1).

(2) (2R,4S)-4-Benzoyloxy-2-methoxycarbonyl-1-phenylsulfonylpyrrolidine $^1$H-NMR (CDCl$_3$) δppm: 2.35 (ddd, J=4, 9.5, 14 Hz, 1H), 2.52 (dt, J=14, 3 Hz, 1H), 3.78 (m, 1H), 3.80 (s, 3H), 3.89 (dd, J=3.5, 12.5 Hz, 1H), 4.42 (dd, J=8, 9.5 Hz, 1H), 5.41 (m, 1H), 7.3–7.4 (m, 5H), 7.5–7.6 (m, 3H), 7.8–7.9 (m, 2H)

Preparation 4

(1) To a solution of (2S,4S)-4-benzoyloxy-1-t-butoxycarbonyl-2-methoxycarbonylpyrrolidine (30.0 g) in methanol (600 ml) was added potassium carbonate (11.9 g) and the mixture was stirred at room temperature for 1 hour. The solution was diluted with ethyl acetate (1 l) and washed with water. The organic phase was washed with brine. The aqueous phase was saturated with sodium chloride, extracted with chloroform and washed with brine. The combined organic extracts were dried over magnesium sulfate and evaporated in vacuo to give an oil. The oil was chromatographed on a silica gel (500 g) column with a mixture of n-hexane and ethyl acetate (1:1) as an eluent to give (2S,4S)-1-t-butoxycarbonyl-4-hydroxy-2-methoxycarbonylpyrrolidine (20.7 g) as colorless crystal.

mp: 59°–62° C.

$^1$H-NMR (CDCl$_3$) δppm: 1.45 (s, 9×3/5H), 1.47 (s, 9×2/5H), 2.10 (m, 1H), 2.33 (m, 1H), 3.5–3.7 (m, 3H), 3.78 (s, 3×3/5H), 3.80 (s, 3×2/5H), 4.35 (m, 1H)

The following compound was obtained according to a similar manner to that of Preparation 4(1).

(2) (2R,4S)-4-Hydroxy-2-methoxycarbonyl-1-phenylsulfonylpyrrolidine $^1$H-NMR (CDCl$_3$) δppm: 2.12 (ddd, J=4.5, 9, 13.5 Hz, 1H), 2.24 (m, 1H), 3.43 (dt, J=11.5, 2 Hz, 1H), 3.62 (dd, J=4, 11.5 Hz), 3.75 (s, 3H), 4.45 (t, J=9 Hz, 1H), 4.47 (m, 1H), 7.5–7.7 (m, 3H), 7.9–8.0 (m, 2H)

Preparation 5

(1) A mixture of (2S,4S)-1-t-butoxycarbonyl-4-methylsulfonyloxy-2-methoxycarbonylpyrrolidine (27.7 g) and sodium azide (10.6 g) in dimethyl sulfoxide (350 ml) was stirred at 90° C. overnight and the solution was diluted with ethyl acetate (600 ml). The solution was washed successively with water and brine and dried over magnesium sulfate. The solvent was evaporated in vacuo to give (2S,4R)-4-azido-1-t-butoxycarbonyl-2-methoxycarbonylpyrrolidine (20.0 g) as a pale brown oil.

$^1$H-NMR (CDCl$_3$) δppm: 1.41 (s, 9×2/3H), 1.47 (s, 9×1/3H), 2.20 (m, 1H), 2.32 (m, 1H), 3.4–3.7 (m, 3H), 3.76 (s, 3H), 4.20 (m, 1H), 4.36 (m, 1H)

The following compounds were obtained according to a similar manner to that of Preparation 5(1).

(2) (2S,4S)-4-Azido-1-t-butoxycarbonyl-2-methoxycarbonylpyrrolidine $^1$H-NMR (CDCl$_3$) δppm: 1.43 (s, 9×3/5H), 1.48 (s, 9×2/5H), 2.14 (t, J=4 Hz, 2/5H), 2.21 (t, J=4 Hz, 3/5H), 2.47 (m, 1H), 3.50 (m, 1H), 3.73 (m, 1H), 3.76 (s, 3H), 4.14 (m, 1H), 4.33 (dd, J=4, 9 Hz, 3/5H), 4.43 (dd, J=4, 9 Hz, 2/5H)

(3) (2R,4S)-4-Azido-2-methoxycarbonyl-1-phenylsulfonylpyrrolidine $^1$H-NMR (CDCl$_3$) δppm: 7.23 (m, 2H), 3.47 (dd, J=3, 12 Hz, 1H), 3.76 (dd, J=5, 12 Hz, 1H), 4.25 (m, 1H), 4.35 (t, J=7 Hz, 1H), 7.5–7.7 (m, 3H), 7.9–8.0 (m, 2H)

(4) (2R,4R)-4-Azido-2-methoxycarbonyl-1-phenylsulfonylpyrrolidine $^1$H NMR (CDCl$_3$) δppm: 2.2–2.4 (m, 2H), 3.35 (dd, J=4, 11 Hz, 1H), 3.67 (dd, J=5.5, 11 Hz, 1H), 3.73 (s, 3H), 4.10 (m, 1H), 4.56 (dd, J=4, 8.5 Hz, 1H), 7.5–7.7 (m, 3H), 7.9–8.0 (m, 2H)

Preparation 6

(1) A solution of (2S,4R)-4-azido-1-t-butoxycarbonyl-2-methoxycarbonylpyrrolidine (112 g) in methanol (870 ml) was hydrogenated under ambient pressure for 5 hours in the presence of 10% palladium on carbon (20.2 g). After removal of the catalyst by filtration, the filtrate was evaporated in vacuo to give (2S,4R)-4-amino-1-t-butoxycarbonyl-2-methoxycarbonylpyrrolidine (93.8 g) as an oil.

$^1$H-NMR (CDCl$_3$) δppm: 1.41 (s, 9×2/3H), 1.46 (s, 9×1/3H), 1.9–2.2 (m, 2H), 3.2–3.4 (m, 1H), 3.6–3.8 (m, 2H), 3.74 (s, 3H), 4.40 (m, 1H)

The following compounds were obtained according to a similar manner to that of Preparation 6(1).

(2) (2S,4S)-4-Amino-1-t-butoxycarbonyl-2-methoxycarbonylpyrrolidine (3) (2R,4S)-4-Amino-2-methoxycarbonyl-1-phenylsulfonylpyrrolidine (4) (2R,4R)-4-Amino-2-methoxycarbonyl-1-phenylsulfonylpyrrolidine

Preparation 7

(1) To a solution of (2S,4R)-4-amino-1-t-butoxycarbonyl-2-methoxycarbonylpyrrolidine (6.04 g) in dichloromethane (60 ml) were added triethylamine (3.44 ml) and p-chlorobenzenesulfonyl chloride (6.26 g) in an ice bath. After being stirred at room temperature overnight, the solution was washed successively with diluted hydrochloric acid, saturated aqueous sodium bicarbonate and brine and dried over magnesium sulfate. The solvent was evaporated in vacuo and the residue was crystallized from n-hexane to give (2S,4R)-1-t-butoxycarbonyl-4-(4-chlorophenylsulfonylamino)-2-methoxycarbonylpyrrolidine (9.13 g) as a pale yellow crystal.

$^1$H-NMR (CDCl$_3$) δppm: 1.37 (s, 9×2/3H), 1.40 (s, 9×1/3H), 2.0–2.4 (m, 2H), 3.20 (m, 1H), 3.63 (m, 1H), 3.95 (m, 1H), 4.30 (m, 1H), 5.0–5.2 (m, 1H), 7.52 (d, J=10 Hz, 2H), 7.83 (d, J=10 Hz, 2H)

The following compounds were obtained according to a similar manner to that of Preparation 7(1).

(2) (2S,4R)-1-t-Butoxycarbonyl-2-methoxycarbonyl-4-phenylsulfonylaminopyrrolidine $^1$H-NMR (CDCl$_3$) δppm: 1.40 (s, 9H), 2.0–2.3 (m, 2H), 3.17 (dd, J=5, 11 Hz, 1H), 3.59 (m, 1H), 3.98 (m, 1H), 4.30 (m, 1H), 4.82 (m, 1H), 7.5–7.7 (m, 3H), 8.8–8.9 (m, 2H)

(3) (2S,4S)-1-t-Butoxycarbonyl-2-methoxycarbonyl-4-phenylsulfonylaminopyrrolidine $^1$H-NMR (CDCl$_3$) δppm: 1.37 (s, 9H), 1.7–1.9 (m, 1H), 2.81 (m, 1H), 3.3–3.5 (m, 2H), 3.74 (s, 3H), 4.03 (m, 1H), 4.20 (m, 1H), 5.93 (broad, 1H), 7.5–7.6 (m, 3H), 7.8–7.9 (m, 2H)

(4) (2R,4S)-2-Methoxycarbonyl-1-phenylsulfonyl-4-phenylsulfonylaminopyrrolidine $^1$H-NMR (CDCl$_3$) δppm: 2.1–2.2 (m, 2H), 3.18 (dd, J=3, 12 Hz, 1H), 3.50 (dd, J=5, 12 Hz, 1H), 3.99 (m, 1H), 4.42 (dd, J=5, 8 Hz, 1H), 4.75 (d, J=7, 1H), 7.5–7.7 (m, 3H), 7.8–7.9 (m, 1H)

(5) (2R,4R)-2-Methoxycarbonyl-1-phenylsulfonyl-4-phenylsulfonylaminopyrrolidine $^1$H NMR (CDCl$_3$) δppm: 1.83 (m, 1H), 2.18 (ddd, J=6, 10, 15 Hz, 1H), 3.2–3.3 (m, 2H), 3.77 (s, 3H), 4.04 (m, 1H), 4.23 (dd, J=2, 6 Hz, 1H), 5.97 (d, J=10 Hz, 1H), 7.4–7.7 (m, 6H), 7.7–7.9 (m, 4H)

Preparation 8

(1) To a solution of (2S,4R)-1-t-butoxycarbonyl-4-(4-chlorophenylsulfonylamino)-2-methoxycarbonylpyrrolidine (9.01 g) in toluene (70 ml) was added dropwise 1.5 molar solution of diisobutylaluminum hydride (61.2 m mol) in tetrahydrofuran (40.8 ml) at −78° C. After the mixture was stirred at −78° C. for 1.5 hours, saturated aqueous potassium sodium tartrate was added to the reaction mixture and the mixture was filtered through Celite. The solid was washed with ethyl acetate and the combined organic solution was washed with brine and dried over magnesium sulfate. The solvent was evaporated in vacuo and the residue was chromatographed on a silica gel column with a mixture of ethyl acetate and n-hexane (1:2–2:1) as an eluent to give (2S,4R)-1-t-butoxycarbonyl-4-(4-chlorophenylsulfonylamino)-2-formylpyrrolidine (5.51 g) as pale yellow crystal.

mp: 120°–122° C.

$^1$H-NMR (CDCl$_3$) δppm: 1.43 (s, 9H), 2.16 (m, 2H), 3.33 (m, 1H), 3.60 (m, 1H), 3.85 (m, 1H), 4.26 (m, 1H), 4.87 (m, 1H), 7.53 (d, J=10 Hz, 2H), 7.82 (d, J=10 Hz, 2H), 9.4–9.6 (m, 1H)

The following compounds were obtained according to a similar manner to that of Preparation 8(1).

(2) (2S,4R)-1-t-Butoxycarbonyl-2-formyl-4-phenylsulfonylaminopyrrolidine $^1$H-NMR (DMSO-d$_6$) δppm: 1.34 (s, 9×3/5H), 1.37 (s, 9×2/5H), 1.94 (m, 2H), 3.17 (m, 1H), 3.38 (m, 1H), 3.67 (m, 1H), 4.15 (m, 1H), 7.6–7.7 (m, 3H) 7.8–7.9 (m, 2H), 8.12 (broad 1H), 9.36 (broad 1H)

(3) (2R,4S)-2-Formyl-1-phenylsulfonyl-4-phenylsulfonylaminopyrrolidine (4) (2R,4R)-2-Formyl-1-phenylsulfonyl-4-phenylsulfonylaminopyrrolidine

Preparation 9

To a solution of (2S,4S)-1-t-butoxycarbonyl-2-methoxycarbonyl-4-phenylsulfonlaminopyrrolidine (10.0 g) in toluene (70 ml) was added dropwise 1.0 molar solution of diisobutylaluminum hydride in toluene (70 ml) at −25° C. and the resulting mixture was stirred at the same temperature for 4 hours. After saturated aqueous ammonium chloride was added to the mixture, the mixture was stirred at room temperature for 1 hour. The mixture was filtered and the filtrate was extracted with ethyl acetate. The organic phase was washed with brine and dried over magnesium sulfate. The solvent was evaporated to give (2S,4S)-1-t-butoxycarbonyl-2-hydroxymethyl-4-phenylsulfonylaminopyrrolidine (9.44 g) as a colorless oil.

$^1$H-NMR (CDCl$_3$) δppm: 1.82 (m, 1H), 2.23 (m, 1H), 3.24 (dd, J=3, 12 Hz, 1H), 3.47 (dd, J=3.5, 12 Hz, 1H), 3.53 (m, 1H), 3.8–3.9 (m, 2H), 4.03 (dd, J=2.5, 11 Hz, 1H), 7.4–7.6 (m, 3H), 7.8–7.9 (m, 2H)

Preparation 10

To a solution of pyridine (8.5 ml) in dichloromethane (150 ml) was added chromium trioxide (5.55 g) in an ice bath and the mixture was stirred at room temperature for 1 hour. To the solution were added Celite and a solution of (2S,4S)-1-t-butoxycarbonyl-2-hydroxymethyl-4-phenylsulfonylaminopyrrolidine (3.4 g) in dichloromethane (20 ml) and the mixture was stirred at room temperature for 1 hour. After being diluted with a mixture of n-hexane and ethyl acetate (1:1, 150 ml), the solution was passed through silica gel and the solvent was evaporated in vacuo to give (2S,4S)-1-t-butoxycarbonyl-2-formyl-4-phenylsulfonylaminopyrrolidine as a pale yellow oil.

EXAMPLE 1

(1) To a solution of (4-carboxybutyl)triphenylphosphonium bromide (17.3 g) in dimethyl sulfoxide (45 ml) was added sodium methylsulfinylmethide [78.0 m mol, prepared from sodium hydride (3.12 g) and dimethyl sulfoxide (45 ml)] and the solution was stirred at room temperature for 20 minutes. To the resulting solution was added (2S,4R)-1-t-butoxycarbonyl-4-(4chlorophenylsulfonylamino)-2-formylpyrrolidine (5.06 g) in dimethyl sulfoxide (30 ml) and the mixture was stirred at room temperature for 2 hours. To the reaction mixture was added water and the aqueous solution was washed with ethyl acetate. The aqueous phase was adjusted to pH 2 with 1N hydrochloric acid and extracted with ethyl acetate. The organic phase was washed successively with water and brine and dried over magnesium sulfate. The solvent was evaporated in vacuo and the residue was chromatographed on a silica gel column with a mixture of chloroform and methanol (40:1) as an eluent to give (2S,4R)-1-t-butoxycarbonyl-2-[(E and Z)-5-carboxy-1-pentenyl]-4-(4-chlorophenylsulfonylamino) pyrrolidine (7.64 g) as a pale brown oil.

$^1$H NMR (CDCl$_3$) δppm: 1.38 (s, 9×2/3H), 1.39 (s, 9×1/3H), 1.7–1.8 (m, 2H), 2.0–2.2 (m, 4H), 2.3–2.5 (m, 2H), 3.30 (m, 1H), 3.45 (dd, J=5, 12 Hz, 1H), 3.86 (m, 1H), 4.58 (m, 1H), 5.2–5.5 (m, 3H), 7.52 (d, J=10 Hz, 1H), 7.83 (d, J=10 Hz, 1H)

The following compounds were obtained according to a similar manner to that of Example 1(1).

(2) (2S,4S)-1-t-Butoxycarbonyl-2-[(E and Z)-5-carboxy-1-pentenyl]-4-phenylsulfonylaminopyrrolidine $^1$H-NMR (CDCl$_3$) δppm: 1.38 (s, 9H), 1.5–1.8 (m, 3H), 2.0–2.1 (m, 3H), 2.3–2.4 (m, 2H), 3.08 (dd, J=6.5, 10.5 Hz, 1H), 3.6–3.8 (m, 2H), 4.44 (m, 1H), 5.2–5.5 (m, 2H), 7.4–7.6 (m, 3H), 7.8–7.9 (m, 2H)

(3) (2S,4R)-1-t-Butoxycarbonyl-2-[(E and Z)-5-carboxy-1-pentenyl]-4-phenylsulfonylaminopyrrolidine $^1$H-NMR (CDCl$_3$) δppm: 1.36 (s, 9H), 1.6–1.8 (m, 3H), 2.0–2.2 (m, 3H), 2.3–2.4 (m, 2H), 3.2–3.5 (m, 2H), 3.85 (m, 1H), 4.57 (m, 1H), 5.1–5.5 (m, 2H), 5.72 (broad 1H), 7.4–7.6 (m, 3H), 7.3–7.4 (m, 2H)

(4) (2R,4S)-2-[(E and Z)-5-Carboxy-1-pentenyl]-1-phenylsulfonyl-4-phenylsulfonylaminopyrrolidine $^1$H-NMR (CDCl$_3$) δppm: 1.5–1.8 (m, 2H), 1.9–2.0 (m, 1H), 2.12 (m, 1H), 2.2–2.4 (m, 2H), 3.4–3.5 (m, 2H), 3.68 (m, 1H), 4.45 (m, 1H), 5.2–5.5 (m, 2H), 6.27 (d, J=6 Hz, 1H), 7.4–7.6 (m, 6H), 7.6–7.9 (m, 4H)

(5) (2R,4R)-2-[(E and Z)-5-Carboxy-1-pentenyl]-1-phenylsulfonyl-4-phenylsulfonylaminopyrrolidine $^1$H-NMR (CDCl$_3$) δppm: 1.4–1.8 (m, 3H), 2.0–2.2 (m, 3H), 2.38 (m, 2H), 3.13 (m, 1H), 3.50 (m, 2H), 4.30 (m, 1H), 4.92 (d, J=6.5 Hz, 1H), 5.3–5.5 (m, 2H), 7.4–7.7 (m, 6H), 7.7–7.9 (m, 4H)

(6) (2S,4R)-2-[(E and Z)-5-Carboxy-1-pentenyl]-1-(4-chlorophenylsulfonyl)-4-(4-chlorophenylsulfonylamino)pyrrolidine
mp: 149°–150° C.

$^1$H-NMR (D$_2$O-NaOD) δppm: 1.4–1.8 (m, 3H), 1.98 (m, 3H), 2.07 (t, J=7.5 Hz, 2H), 2.77 (t, J=9 Hz, 1H), 3.28 (t, J=9 Hz, 1H), 3.56 (m, 1H) 4.43 (m, 1H), 5.0–5.3 (m, 2H), 7.36 (d, J=8 Hz, 2H), 7.4–7.7 (m, 6H)

(7) (2S,4R)-2-[(E and Z)-5-Carboxy-1-pentenyl]-4-(4-chlorophenylsulfonylamino)-1-phenylsulfonylpyrrolidine (8) (2S,4R)-2-[(E and Z)-5-Carboxy-1-pentenyl]-4-(4-chlorophenylsulfonylamino)-1-(4-methylphenylsulfonyl)pyrrolidine
mp: 116°–119° C.

$^1$H-NMR (CDCl$_3$) δppm: 1.6–1.8 (m, 3H), 2.0–2.2 (m, 3H), 2.3–2.5 (m, 2H), 2.45 (s, 3H), 3.3–3.5 (m, 2H), 3.78 (m, 1H), 4.52 (m, 1H), 5.2–5.6 (m, 3H), 7.3–7.4 (m, 2H), 7.5 (m, 2H), 7.6–7.8 (m, 4H)

(9) (2S,4R)-2-[(E and Z)-5-Carboxy-1-pentenyl]-4-(4-chlorophenylsulfonylamino)-1-(4-trifluoromethylphenylsulfonyl)pyrrolidine
mp: 152°–154° C.

$^1$H-NMR (CDCl$_3$) δppm: 1.5–1.9 (m, 3H), 2.0–2.2 (m, 3H), 2.3–2.5 (m, 2H), 3.46 (m, 1H), 3.62 (m, 1H), 3.70 (m, 1H), 4.63 (m, 1H), 5.2–5.3 (m, 1H), 5.4–5.6 (m, 2H), 7.4–7.5 (m, 2H), 7.7–7.8 (m, 4H), 7.9–8.0 (m, 2H)

(10) (2S,4R)-2-[(E and Z)-5-Carboxy-1-pentenyl[-4-(4-chlorophenylsulfonylamino)-1-(4-methoxyphenylsulfonyl)pyrrolidine
mp: 158°–160° C.

$^1$H-NMR (CDCl$_3$) δppm: 1.6–1.9 (m, 3H), 2.0–2.2 (m, 3H), 2.3–2.5 (m, 2H), 3.3–3.5 (m, 2H), 3.75 (m, 1H), 3.90 (s, 3H), 4.48 (m, 1H), 5.15 (d, J=7 Hz, 1H), 5.2–5.5 (m, 2H), 7.00 (d, J=9 Hz, 2H), 7.4–7.5 (m, 2H), 7.7–7.8 (m, 4H)

(11) (2S,4R)-2-[(E and Z)-5-Carboxy-1-pentenyl]-4-(4-chlorophenylsulfonylamino)-1-(4-fluorophenylsulfonyl)pyrrolidine
mp: 78°–82° C.

$^1$H-NMR (CDCl$_3$) δppm: 1.6–1.9 (m, 3H), 2.0–2.2 (m, 3H), 2.3–2.4 (m, 2H), 3.4–3.5 (m, 2H), 3.72 (m, 1H), 4.57 (m, 1H), 5.25 (m, 1H), 5.4–5.6 (m, 2H), 7.1–7.2 (m, 2H), 7.5–7.6 (m, 2H), 7.71–7.9 (m, 4H)

(12) (2S,4R)-1-(4-Bromophenylsulfonyl)-2-[(E and Z)-5-carboxy-1-pentenyl]-4-(4-chlorophenylsulfonylamino)pyrrolidine
mp: 116°–120° C.

$^1$H-NMR (CDCl$_3$) δppm: 1.5–1.9 (m, 3H), 2.0–2.2 (m, 3H), 2.3–2.5 (m, 2H), 3.4–3.5 (m, 2H), 3.75 (m, 1H), 4.57 (m, 1H), 5.25 (m, 1H), 5.4–5.5 (m, 2H), 7.4–7.5 (m, 2H), 7.6–7.7 (m, 4H), 7.7–7.8 (m, 2H)

(13) (2S,4R)-2-[(E and Z)-5-Carboxy-1-pentenyl]-4-(4-chlorophenylsulfonylamino)-1-(4-nitrophenylsulfonyl)pyrrolidine chlorophenylsulfonylamino)-1-(4-nitrophenylsulfonyl)pyrrolidine
mp: 70°–73° C.

$^1$H-NMR (CDCl$_3$) δppm: 1.6–1.9 (4H, m), 2.03 (1H, m), 2.21 (1H, m), 2.3–2.5 (2H, m), 3.48 (1H, m), 3.6–3.8 (2H, m), 4.62 (1H, m), 5.1–5.3 (2H, m), 5.55 (1H, m), 7.4–7.5 (2H, m), 7.7–7.8 (2H, m), 7.9–8.0 (2H, m), 8.3–8.4 (2H, m)

(14) (2S,4R)-2-[(E and Z)-5-Carboxy-1-pentenyl]-1-phenylsulfonyl-4-pyhenylsulfonylaminopyrrolidine $^1$H-NMR (CDCl$_3$) δppm: 1.6–1.8 (3H, m), 1.9–2.2 (3H, m), 2.38 (2H, m), 3.3–3.5 (2H, m), 3.79 (1H, m), 4.52 (1H, m), 5.09 (1H, broad), 5.2–5.6 (2H, m), 7.4–7.6 (3H, m), 7.8–7.9 (2H, m)

(15) (2S,4R)-2-[(E and Z)-5-Carboxy-1-pentenyl]-1-(4-chlorophenylsulfonyl)-4-phenylsulfonylaminopyrrolidine

(16) (2S,4S)-2-[(E and Z)-5-Carboxy-1-pentenyl]-1-phenylsulfonyl-4-phenylsulfonylaminopyrrolidine

(17) (2S,4R)-2-[(E and Z)-5-Carboxy-1-pentenyl]-1-phenylcarbamoyl-4-phenylsulfonylaminopyrrolidine

(18) (2S,4R)-1-t-Butoxycarbonyl-2-[(E and Z)-4-carboxy-1-butenyl]-4-(4-chlorophenylsulfonylamino)pyrrolidine $^1$H-NMR (CDCl$_3$) δppm: 1.39 (9H, s), 1.7–1.9 (2H, m), 2.3–2.5 (4H, m), 3.3–3.5 (2H, m), 3.85 (1H, m), 4.67 (1H, m), 5.2–5.5 (2H, m), 5.88 (1H, m), 7.50 (2H, d, J=8 Hz), 7.85 (2H, d, J=8 Hz)

EXAMPLE 2

(1) A solution of (2S,4R)-1-t-butoxycarbonyl-2-[(E and Z)-5-carboxy-1-pentenyl]-4-(4-chlorophenylsulfonylamino)pyrrolidine (7.63 g) in 75% aqueous trifluoroacetic acid (48 ml) was stirred at room temperature for 40 minutes and the solvent was evaporated in vacuo. To the residue was added toluene (50 ml) and the solvent was evaporated in vacuo to give (2S,4R)-2-[(E and Z)-5-carboxy-1-pentenyl]-4-(4-chlorophenylsulfonylamino)pyrrolidine trifluoroacetate (7.85 g) as a brown oil.

$^1$H-NMR (CDCl$_3$) δppm: 1.70 (2H, m), 2.0–2.2 (4H, m), 2.37 (2H, t, J=7 Hz), 3.36 (1H, m), 3.58 (1H, dd, J=5, 12 Hz), 4.06 (1H, m), 4.60 (1H, m), 5.45 (1H, m), 5.85 (1H, m), 7.68 (2H, d, J=9 Hz), 7.88 (2H, d, J=9 Hz)

The following compounds were obtained according to a similar manner to that of Example 2(1).

(2) (2S,4R)-2-[(E and Z)-5-Carboxy-1-pentenyl]-4-phenylsulfonylaminopyrrglidine trifluoroacetate $^1$H-NMR (D$_2$O) δppm: 1.7–1.9 (4H, m), 2.1–2.3 (2H, m), 2.3–2.4 (2H, m), 3.3–3.6 (2H, m), 4.07 (1H, m), 4.80 (1H, m), 4.46 (1H, m), 5.80 (1H, m), 7.5–7.7 (3H, m), 7.8–7.9 (2H, m) (3) (2S,4S)-2-[(E and Z)-5-Carboxy-1-pentenyl]-4-phenylsulfonylaminopyrrolidine trifluoroacetate (4) (2S,4R)-4-(4-Chlorophenylsulfonylamino)-2-[(E)-2-(4-methoxycarbonylphenyl)vinyl]pyrrolidine mp: 145°–147° C.

$^1$H-NMR (CDCl$_3$) δppm: 1.8–2.1 (2H, m), 2.85 (1H, dd, J=4, 11 Hz), 3.28 (1H, dd, J=6, 11 Hz), 3.90 (3H, s), 3.8–4.0 (2H, m), 6.20 (1H, dd, J=7, 16 Hz), 6.51 (1H, d, J=16 Hz), 7.36 (2H, d, J=8.5 Hz), 7.49 (2H, d, J=8.5 Hz), 7.83 (2H, d, J=8.5 Hz), 7.94 (2H, d, J=8.5 Hz)

EXAMPLE 3

(1) To a solution of (2S,4R)-2-[(E and Z)-5-carboxy-1-pentenyl]-4-(4-chlorophenylsulfonylamino)pyrrolidine trifluoroacetate (7.85 g) in dichloromethane (80 ml) were added triethylamine (8.98 ml) and 4-chlorobenzenesulfonyl chloride (3.40 g) under an ice bath cooling and the mixture was stirred at the same temperature for 1.5 hours. The solution was washed successively with diluted hydrochloric acid and water and the organic phase was extracted with 1N aqueous sodium hydroxide. The aqueous phase was washed with ethyl acetate and adjusted to pH 3 with 3N hydrochloric acid. The aqueous solution was extracted with ethyl acetate and the organic phase was washed successively with water and brine and dried over magnesium sulfate. The solvent was evaporated in vacuo and the residue was chromatographed on a silica gel column with chloroform as an eluent to give (2S,4R)-2-[(E and Z)-5-carboxy-1-pentenyl]-1-(4-chlorophenylsulfonyl)-4-(4-chlorophenylsulfonylamino) pyrrolidine (2.03 g) as a pale yellow crystal.

mp: 149°–150° C.

$^1$H-NMR (D$_2$O-NaOD) δppm: 1.4–1.8 (m, 3H), 1.98 (m, 3H), 2.07 (t, J=7.5 Hz, 2H), 2.77 (t, J=9 Hz, 1H), 3.28 (t, J=9 Hz, 1H), 3.56 (m, 1H), 4.43 (m, 1H), 5.0–5.3 (m, 2H), 7.36 (d, J=8 Hz, 2H), 7.4–7.7 (m, 6H)

The following compounds were obtained according to a similar manner to that of Example 3(1).

(2) (2S,4R)-2-[(E and Z)-5-Carboxy-1-pentenyl]-4-(4-chlorophenylsulfonylamino)-1-phenylsulfonylpyrrolidine (3) (2S,4R)-2-[(E and Z)-5-Carboxy-1-pentenyl]-4-(4-chlorophenylsulfonylamino)-1-(4-methylphenylsulfonyl)pyrrolidine mp: 116°–119° C.

$^1$H-NMR (CDCl$_3$) δppm: 1.6–1.8 (m, 3H), 2.0–2.2 (m, 3H), 2.3–2.5 (m, 2H), 2.45 (s, 3H), 3.3–3.5 (m, 2H), 3.78 (m, 1H), 4.52 (m, 1H), 5.2–5.6 (m, 3H), 7.3–7.4 (m, 2H), 7.5 (m, 2H), 7.6–7.8 (m, 4H)

(4) (2S,4R)-2-[(E and Z)-5-Carboxy-1-pentenyl]-4-(4-chlorophenylsulfonylamino)-1-(4-trifluoromethylphenylsulfonyl)pyrrolidine mp: 152°–154° C.

$^1$H-NMR (CDCl$_3$) δppm: 1.5–1.9 (m, 3H), 2.0–2.2 (m, 3H), 2.3–2.5 (m, 2H), 3.46 (m, 1H), 3.62 (m, 1H), 3.70 (m, 1H), 4.63 (m, 1H), 5.2–5.3 (m, 1H), 5.4–5.6 (m, 2H), 7.4–7.5 (m, 2H), 7.7–7.8 (m, 4H), 7.9–8.0 (m, 2H) (5) (2S,4R)-2-[(E and Z)-5-Carboxy-1-pentenyl]-4-(4-chlorophenylsulfonylamino)-1-(4-methoxyphenylsulfonyl)pyrrolidine mp: 158°–160° C.

$^1$H-NMR (CDCl$_3$) δppm: 1.6–1.9 (m, 3H), 2.0–2.2 (m, 3H), 2.3–2.5 (m, 2H), 3.3–3.5 (m, 2H), 3.75 (m, 1H), 3.90 (s, 3H), 4.48 (m, 1H), 5.15 (d, J=7 Hz, 1H), 5.2–5.5 (m, 2H), 7.00 (d, J=9 Hz, 2H), 7.4–7.5 (m, 2H), 7.7–7.8 (m, 4H)

(6) (2S,4R)-2-[(E and Z)-5-Carboxy-1-pentenyl]-4(4-chlorophenylsulfonylamino)-1-(4-fluorophenylsulfonyl)pyrrolidine mp: 78°–82° C.

$^1$H-NMR (CDCl$_3$) δppm: 1.6–1.9 (m, 3H), 2.0–2.2 (m, 3H), 2.3–2.4 (m, 2H), 3.4–3.5 (m, 2H), 3.72 (m, 1H), 4.57 (m, 1H), 5.25 (m, 1H), 5.4–5.6 (m, 2H), 7.1–7.2 (m, 2H), 7.5–7.6 (m, 2H), 7.7–7.9 (m, 4H)

(7) (2S,4R)-1-(4-Bromophenylsulfonyl)-2-[(E and Z)-5-carboxy-1-pentenyl]-4-(4-chlorophenylsulfonylamino)pyrrolidine mp: 116°–120° C.

$^1$H-NMR (CDCl$_3$) δppm: 1.5–1.9 (m, 3H), 2.0–2.2 (m, 3H), 2.3–2.5 (m, 2H), 3.4–3.5 (m, 2H), 3.75 (m, 1H), 4.57 (m, 1H), 5.25 (m, 1H), 5.4–5.5 (m, 2H), 7.4–7.5 (m, 2H), 7.6–7.7 (m, 4H), 7.7–7.8 (m, 2H)

(8) (2S,4R)-2-[(E and Z)-5-Carboxy-1-pentenyl]-4-(4-chlorophenylsulfonylamino)-1-(4-nitrophenylsulfonyl)pyrrolidine mp: 70°–73° C.

$^1$H-NMR (CDCl$_3$) δppm : 1.6–1.9 (m, 4H), 2.03 (m, 1H), 2.21 (m, 1H), 2.3–2.5 (m, 2H), 3.48 (m, 1H), 3.6–3.8 (m, 2H), 4.62 (m, 1H), 5.1–5.3 (m, 2H), 5.55 (m, 1H), 7.4–7.5 (m, 2H), 7.7–7.8 (m, 2H), 7.9–8.0 (m, 2H), 8.3–8.4 (m, 2H) (9) (2S,4R)-2-[(E and Z)-5-Carboxy-1-pentenyl]-1-phenylsulfonyl-4-phenylsulfonylaminopyrrolidine $^1$H-NMR (CDCl$_3$) δppm: 1.6–1.8 (m, 3H), 1.9–2.2 (m, 3H), 2.38 (m, 2H), 3.3–3.5 (m, 2H), 3.79 (m, 1H), 4.52 (m, 1H), 5.09 (broad 1H), 5.2–5.6 (m, 2H), 7.4–7.6 (m, 3H), 7.8–7.9 (m, 2H)

(10) (2S,4R)-2-[(E and Z)-5-Carboxy-1-pentenyl]-1-(4-chlorophenylsulfonyl)-4-phenylsulfonylaminopyrrolidine

(11) (2S,4S)-2-[(E and Z)-5-Carboxy-1-pentenyl]-1-phenylsulfonyl-4-phenylsulfonylaminopyrrolidine

(12) (2S,4R)-1-t-Butoxycarbonyl-2-[(E and Z)-5-carboxy-1-pentenyl]-4-(4-chlorophenylsulfonylamino)pyrrolidine $^1$H-NMR (CDCl$_3$) δppm: 1.38 (s, 9×2/3H), 1.39 (s, 9×1/3H), 1.7–1.8 (m, 2H), 2.0–2.2 (m, 4H), 2.3–2.5 (m, 2H), 3.30 (m, 1H), 3.45 (dd, J=5, 12 Hz, 1H), 3.86 (m, 1H), 4.58 (m, 1H), 5.2–5.5 (m, 3H), 7.52 (d, J=10 Hz, 1H), 7.83 (d, J=10 Hz, 1H)

(13) (2S,4S)-1-t-Butoxycarbonyl-2-[(E and Z)-5-carboxy-1-pentenyl]-4-phenylsulfonylaminopyrrolidine $^1$H-NMR (CDCl$_3$) δppm: 1.38 (s, 9H), 1.5–1.8 (m, 3H), 2.0–2.1 (m, 3H), 2.3–2.4 (m, 2H), 3.08 (dd, J=6.5, 10.5 Hz, 1H), 3.6–3.8 (m, 2H), 4.44 (m, 1H), 5.2–5.5 (m, 2H), 7.4–7.6 (m, 3H), 7.8–7.9 (m, 2H)

(14) (2S,4R)-1-t-Butoxycarbonyl-2-[(E and Z)-5-carboxy-1-pentenyl]-4-phenylsulfonylaminopyrrolidine $^1$H-NMR (CDCl$_3$) δppm: 1.36 (s, 9H), 1.6–1.8 (m, 3H), 2.0–2.2 (m, 3H), 2.3–2.4 (m, 2H), 3.2–3.5 (m, 2H), 3.85 (m, 1H), 4.57 (m, 1H), 5.1–5.5 (m, 2H), 5.72 (broad 1H), 7.4–7.6 (m, 3H), 7.3–7.4 (m, 2H)

(15) (2R,4S)-2-[(E and Z)-5-Carboxy-1-pentenyl]-1-phenylsulfonyl-4-phenylsulfonylaminopyrrolidine $^1$H-NMR (CDCl$_3$) δppm: 1.5–1.8 (m, 2H), 1.9–2.0 (m, 1H), 2.12 (m, 1H), 2.2–2.4 (m, 2H), 3.4–3.5 (m, 2H), 3.68 (m, 1H), 4.45 (m, 1H), 5.2–5.5 (m, 2H), 6.27 (d, J=6 Hz, 1H), 7.4–7.6 (m, 6H), 7.6–7.91 (m, 4H)

(16) (2R,4R)-2-[(E and Z)-5-Carboxy-1-pentenyl]-1-phenylsulfonyl-4-phenylsulfonylaminopyrrolidine $^1$H-NMR (CDCl$_3$) δppm: 1.4–1.8 (m, 3H), 2.0–2.2 (m, 3H), 2.38 (m, 2H), 3.13 (m, 1H), 3.50 (m, 2H), 4.30 (m, 1H), 4.92 (d, J=6.5 Hz, 1H), 5.3–5.5 (m, 2H), 7.4–7.7 (m, 6H), 7.7–7.9 (m, 4H)

(17) (2S,4R)-1-Butylsulfonyl-2-[(E and Z)-5-carboxy-1-pentenyl]-4-(4-chlorophenylsulfonylamino)pyrrolidine $^1$H-NMR (CDCl$_3$) δppm: 0.91 (3H, t, J=7 Hz), 1.3–1.5 (3H, m), 1.6–1.9 (4H, m), 2.1–2.3 (3H, m), 2.3–2.4 (2H, m), 2.95 (2H, m), 3.30 (1H, m), 3.50 (1H, m), 4.73 (1H, m), 5.2–5.4 (1H, m), 5.4–5.7 (1H, m), 5.77 (1H, d, J=6.5 Hz), 7.51 (2H, d, J=9 Hz), 7.83 (2H, d, J=9 Hz)

(18) (2S,4R)-1-Benzoyl-2-[(E and Z)-5-carboxy-1-pentenyl]-4-(4-chlorophenylsulfonylamino)pyrrolidine $^1$H-NMR (CDCl$_3$) δppm: 1.7–2.0 (4H, m), 2.1–2.5 (5H, m), 3.33 (1H, m), 3.58 (1H, m), 3.92 (1H, m), 5.1–5.4 (2H, m), 7.3–7.5 (7H, m), 7.6–7.8 (2H, m)

(19) (2S,4R)-2-[(E and Z)-5-Carboxy-1-pentenyl]-1-(4-methoxyphenylsulfonyl)-4-phenylsulfonylaminopyrrolidine mp: 130°–131° C.

$^1$H-NMR (D$_2$O-N$_a$OD) δppm: 1.3–1.4 (4H, m), 1.7–2.0 (4H, m), 2.58 (1H, m), 3.19 (1H, m), 3.47 (1H, m), 3.76 (3H, s), 4.20 (1H, m), 4.9–5.2 (2H, m), 6.9–7.0 (2H, m), 7.3–7.4 (2H, m), 7.5–7.6 (4H, m)

(20) (2S,4R)-2-[(E and Z)-5-Carboxy-1-pentenyl]-1(4-methylphenylsulfonyl)-4-phenylsulfonylaminopyrrolidine

(21) (2S,4R)-1-(4-Bromophenylsulfonyl)-2-[(E and Z)--carboxy-1-pentenyl]-4-phenylsulfonylaminopyrrolidine

(22) (2S,4R)-2-[(E and Z)-5-Carboxy-1-pentenyl]-phenylsulfonylamino-1-(4-trifluoromethylphenylsulfonyl)pyrrolidine mp: 108°–110° C.

$^1$H-NMR (D$_2$O-NaOD) δppm: 1.5–1.7 (3H, m), 1.7–1.9 (2H, m), 1.9–2.2 (4H, m), 3.34 (1H, m), 3.49 (1H, m), 4.43 (1H, m), 5.3–5.6 (2H, m), 7.3–7.5 (3H, m), 7.6–8.0 (6H, m)

(23) (2S,4R)-2-[(E and Z)-5-Carboxy-1-pentenyl]-1-(4-nitrophenylsulfonyl)-4-phenylsulfonylaminopyrrolidine mp: 132°–134° C.

$^1$H-NMR (CDCl$_3$) δppm: 1.6–1.9 (3H, m), 1.9–2.1 (2H, m), 2.1–2.2 (2H, m), 2.3–2.4 (2H, m), 3.42 (1H, m), 3.63 (1H, m), 4.57 (1H, m), 5.3–5.6 (2H, m), 7.4–7.6 (3H, m), 7.7–7.8 (2H, m), 7.9–8.0 (2H, m), 8.3–8.4 (2H, m)

(24) (2S,4R)-2-[(E and Z)-5-Carboxy-1-pentenyl]-1-(4-fluorophenylsulfonyl)-4-phenylsulfonylaminopyrrolidine

(25) (2S,4R)-1-Butylsulfonyl-2-[(E and Z)-5-carboxy-1-pentenyl]-4-phenylsulfonylaminopyrrolidine

(26) (2S,4R)-2-[(E and Z)-5-Carboxy-1-pentenyl]-phenylsulfonylamino-1-(2-thienylsulfonyl)pyrrolidine

(27) (2S,4R)-2-[(E and Z)-4-Carboxy-1-butenyl]-1-(4-chlorophenylsulfonyl)-4-(4-chlorophenylsulfonylamino)pyrrolidine $^1$H-NMR (CDCl$_3$) δppm: 1.6–1.9 (2H, m), 2.04 (1H, m), 2.3–2.5 (3H, m), 3.3–3.5 (2H, m), 3.77 (1H, m), 4.68 (1H, m), 5.23 (1H, m), 5.3–5.6 (1H, m), 5.76 (1H, m), 7.3–7.5 (4H, m), 7.6–7.9 (4H, m)

(28) (2S,4R)-1-(4-Chlorophenylsulfonyl)-4-(4-chlorophenylsulfonylamino)-2-[(E)-2-(4-methoxycarbonylphenyl)vinyl]pyrrolidine mp: 168°–169° C.

$^1$H-NMR (CDCl$_3$) δppm: 1.9–2.1 (2H, m), 3.32 (1H, dd, J=4, 11 Hz), 3.49 (1H, dd, J=5.5, 11 Hz), 3.92 (3H, s), 4.47 (1H, q, J=7 Hz), 4.87 (1H, d, J=7.5 Hz), 5.92 (1H, dd, J=7.5, 16 Hz), 6.47 (1H, d, J=16 Hz), 7.28 (2H, d, J=8.5 Hz), 7.41 (2H, d, J=8.5 Hz), 7.51 (2H, d, J=8.5 Hz), 7.69 (2H, d, J=8.5 Hz), 7.74 (2H, d, J=8.5 Hz), 7.79 (2H, d, J=8.5 Hz), 7.97 (2H, d, J=8.5 Hz)

EXAMPLE 4

A mixture of (2S,4R)-2-[(E and Z)-5-carboxy-1-pentenyl]-4-phenylsulfonylaminopyrrolidine (169 mg), triethylamine (0.070 ml) and phenyl isocyanate (0.060 ml) in methanol (5 ml) was stirred at room temperature overnight and water was added to the solution. The solution was extracted with chloroform and organic phase was washed with brine. After the solution was dried over magnesium sulfate, the solvent was evaporated in vacuo and the residue was chromatographed on a silica gel column with a mixture of chloroform and methanol (40:1) as an eluent to give (2S,4R)-2-[(E and Z)-5-carboxy-1-pentenyl]-1-phenylcarbamoyl-4-phenylsulfonylaminopyrrolidine (51 mg) as an oil.

EXAMPLE 5

(1) A solution of (2S,4R)-2-[(E and Z)-5-carboxy-1-pentenyl]-1-(4-chlorophenylsulfonyl)-4-(4-chlorophenylsulfonylamino)pyrrolidine (300 mg) in a mixture of methanol (0.5 ml), 1N aqueous sodium hydroxide (0.6 ml) and water was stirred at room temperature for 30 minutes and the solution was washed with dichloromethane. The aqueous phase was subjected to a column of "Diaion HP 20" [Trademark: prepared by Mitsubishi Chemical Industries] and washed with water. The elution was carried out with 50% aqueous methanol and the eluate was lyophilized to give sodium salt of (2S,4R)-2-[(E and Z)-5-carboxy-1-pentenyl]-1-(4-chlorophenylsulfonyl)-4-(4-chlorophenylsulfonylamino)pyrrolidine (220 mg) as a white powder.

mp: 114°–121° C. (dec.)

1H-NMR (D$_2$O-NaOD) δppm: 1.4–1.7 (m, 4H), 1.9–2.2 (m, 4H), 2.78 (m, 1H), 3.37 (m, 1H), 3.63 (m, 1H), 4.45 (m, 1H), 5.2–5.5 (m, 2H), 7.4–7.8 (m, 8H)

The following compounds were obtained according to a similar manner to that of Example 5(1).

(2) Sodium salt of (2S,4R)-2-[(E and Z)-5-carboxy-1-pentenyl]-4-(4-chlorophenylsulfonylamino)-1-phenylsulfonylpyrrolidine $^1$H-NMR (D$_2$O) δppm: 1.60 (m, 2H), 1.83 (m, 2H), 2.03 (m, 2H), 2.16 (t, J=7 Hz, 2H), 3.39 (m, 1H), 3.55 (m, 1H), 3.71 (m, 1H), 4.38 (q, J=8.5 Hz, 1H), 5.3–5.6 (m, 2H), 7.6–7.9 (m, 9H)

(3) Sodium salt of (2S,4R)-2-(E and Z)-5-Carboxy-1-pentenyl]-1-phenylsulfonyl-4phenylsulfonylaminopyrrolidine 1H-NMR (D$_2$O) δppm: 1.5–1.7 (m, 2H), 1.7–1.8 (m, 2H), 1.9–2.1 (m, 2H), 2.15 (m, 2H), 3.33 (m, 1H), 3.57 (m, 1H), 3.70 (m, 1H), 4.38 (m, 1H), 5.3–5.6 (m, 2H), 7.5–7.9 (m, 10H)

(4) Sodium salt of (2S,4R)-2-[(E and Z)-5-Carboxy-1-pentenyl]-1-(4-chlorophenylsulfonyl)-4-phenylsulfonylaminopyrrolidine $^1$H-NMR (D$_2$O) δppm: 1.4–1.6 (m, 2H), 1.74 (m, 1H), 1.89 (m, 1H), 1.9–2.1 (m, 2H), 2.12 (m, 2H), 3.2–3.5 (m, 2H), 3.62 (m, 1H), 4.42 (m, 1H), 5.1–5.3 (m, 1H), 5.3–5.6 (m, 1H), 7.4–7.7 (m, 9H)

(5) Sodium salt of (2S,4R)-2-[(E and Z)-5-carboxy-1-pentenyl]-1-phenylcarbamoyl-4-phenylsulfonylaminopyrrolidine $^1$H-NMR (D$_2$O) δppm: 1.5–1.7 (m, 2H), 1.78 (m, 1H), 2.0–2.2 (m, 5H), 3.28 (dd, J=5, 11 Hz, 1H), 3.57 (dd, J=6, 11 Hz, 1H), 3.88 (m, 1H), 4.72 (m, 1H), 5.3–5.6 (m, 2H), 7.1–7.3 (m, 3H), 7.3–7.4 (m, 2H), 7.5–7.6 (m, 3H), 7.8–7.9 (m, 2H)

(6) Sodium salt of (2S,4S)-2-[(E and Z)-5-carboxy-1-pentenyl]-1-phenylsulfonyl-4-phenylsulfonylaminopyrrolidine $^1$H-NMR (CDCl$_3$) δppm: 1.4–1.7 (m, 4H), 2.0–2.2 (m, 4H), 2.9–3.2 (m, 3H), 3.37 (dd, J=6, 12 Hz), 4.28 (m, 1H), 5.4–5.5 (m, 2H), 7.6–7.8 (m, 10H)

(7) Sodium salt of (2R,4S)-2-[(E and Z)-5-Carboxy-1-pentenyl]-1-phenylsulfonyl-4-phenylsulfonylaminopyrrolidine $^1$H-NMR (D$_2$O) δppm: 1.5–1.7 (m, 2H), 1.81 (m, 1H), 2.03 (m, 1H), 2.1–2.2 (m, 2H), 3.40 (m, 1H), 3.56 (dd, J=4.5, 11.5 Hz, 1H), 3.7 (m, 1H), 4.38 (m, 1H), 5.3–5.6 (m, 2H), 7.5–7.9 (m, 10H)

(8) Sodium salt of (2R,4R)-2-[(E and Z)-5-Carboxy-1-pentenyl]-1-phenylsulfonyl-4-phenylsulfonylaminopyrrolidine $^1$H-NMR (D$_2$O) δppm: 1.4–1.7 (m, 4H), 2.0–2.2 (m, 4H), 2.9–3.2 (m, 2H), 3.37 (m, 1H), 4.28 (m, 1H), 5.4–5.6 (m, 2H), 7.5–7.8 (m, 10H)

(9) Sodium salt of (2S,4R)-1-butylsulfonyl-2-[(E and Z)-5-carboxy-1-pentenyl]-4-(4-chlorophenylsulfonylamino)pyrrolidine $^1$H-NMR (D$_2$O) δppm: 0.92 (3H, t, J=7 Hz), 1.4–1.5 (3H, m), 1.5–1.8 (4H, m), 2.0–2.2 (5H, m), 3.0–3.2 (2H, m), 3.4–3.5 (2H, m), 3.83 (1H, m), 4.65 (1H, m), 5.3–5.7 (2H, m), 7.61 (2H, d, J=9 Hz), 7.84 (2H, d, J=9 Hz)

(10) Sodium salt of (2S,4R)-1-benzoyl-2-[(E and Z)-5-carboxy-1-pentenyl]-4-(4-chlorophenylsulfonylamino)pyrrolidine $^1$H-NMR (D$_2$O) δppm: 1.1–1.4 (1H, m), 1.6–1.8 (1H, m), 1.90 (1H, m), 2.06 (1H, m), 2.1–2.3 (3H, m), 3.02 (1H, m), 3.5–3.7 (1H, m), 3.98 (1H, m), 4.7–5.1 (2H, m), 5.37 (1H, m), 5.5–5.7 (1H, m), 7.3–7.5 (5H, m), 7.62 (2H, m), 7.90 (2H, m)

(11) Sodium salt of (2S,4R)-2-[(E and Z)-5-carboxy-1-pentenyl]-1-(4-methylphenylsulfonyl)-4-phenylsulfonylaminopyrrolidine mp: 109°–113° C.

$^1$H-NMR (D$_2$O) δppm: 1.5–1.7 (3H, m), 1.7–1.9 (2H, m), 1.9–2.1 (2H, m), 2.1–2.2 (2H, m), 2.47 (3H, s), 3.53 (1H, m), 3.68 (1H, m), 4.33 (1H, m), 5.3–5.6 (2H, m), 7.4–7.8 (9H, m)

(12) Sodium salt of (2S,4R)-1-(4-bromophenylsulfonyl)-2-[(E and Z)-5-carboxy-1-pentenyl]-4-phenylsulfonylaminopyrrolidine mp: 108°–112° C.

$^1$H-NMR (D$_2$O) δppm: 1.4–1.7 (3H, m), 1.8–2.2 (6H, m), 3.51 (1H, m), 3.64 (1H, m), 4.37 (1H, m), 5.3–5.6 (2H, m), 7.6–7.9 (5H, m)

(13) Sodium salt of (2S,4R)-2-[(E and Z)-5-carboxy-1-pentenyl]-1-(4-fluorophenylsulfonyl)-4-phenylsulfonylaminopyrrolidine mp: 94°–98° C.

$^1$H-NMR (D$_2$O) δppm: 1.3–1.6 (4H, m), 1.72 (1H, m), 1.8–2.1 (3H, m), 2.70 (1H, m), 3.22 (1H, m), 3.47 (1H, m), 4.36 (1H, m), 5.3–5.7 (2H, m), 7.3–7.4 (5H, m), 7.5–7.6 (2H, m), 7.7–7.8 (2H, m)

(14) Sodium salt of (2S,4R)-1-butylsulfonyl-2-[(E and Z)-5-carboxy-1-pentenyl]-4-phenylsulfonylaminopyrrolidine mp: 96°–98° C.

$^1$H-NMR (D$_2$O) δppm: 0.78 (3H, t, J=7 Hz), 1.2–1.4 (2H, m), 1.4–1.7 (5H, m), 1.8–2.1 (5H, m), 2.86 (1H, m), 3.03 (2H, m), 3.24 (1H, m), 3.56 (1H, m), 4.50 (1H, m), 5.2–5.4 (2H, m), 7.4–7.5 (3H, m), 7.6–7.7 (2H, m)

(15) Sodium salt of (2S,4R)-2-[(E and Z)-5-carboxy-1-pentenyl]-4-phenylsulfonylamino-1-(2-thienylsulfonyl)-pyrrolidine mp: 110°–112° C.

$^1$H-NMR (D$_2$O) δppm: 1.5–1.7 (3H, m), 1.8–2.0 (2H, m), 2.0–2.2 (4H, m), 3.45 (1H, m), 3.61 (1H, m), 4.47 (1H, m), 5.3–5.6 (2H, m), 7.31 (1H, m), 7.6–7.8 (6H, m), 7.92 (1H, m)

(16) Sodium salt of (2S,4R)-2-[(E and Z)-4-carboxy-1-butenyl]-1-(4-chlorophenylsulfonyl)-4-(4-chlorophenylsulfonylamino)pyrrolidine mp: 60°–64° C.

$^1$H-NMR (D$_2$O) δppm: 1.6–1.8 (2H, m), 2.0–2.4 (4H, m), 3.18 (1H, m), 3.5–3.7 (2H, m), 4.14 (1H, m), 4.8–5.0 (1H, m), 5.1–5.4 (1H, m), 7.2–7.4 (4H, m), 7.6–7.9 (4H, m)

EXAMPLE 6

The crude (2S,4R)-2-[(E and Z)-5-carboxy-1-pentenyl]-1-(4-chlorophenylsulfonyl)-4-(4-chlorophenylsulfonylamino)pyrrolidine, which was obtained by treating (2S,4R)-2-[(E and Z)-5-carboxy-1-pentenyl]-4-(4-chlorophenylsulfonylamino)pyrrolidine trifluoroacetate (8.14 g) according to a similar manner to that of Example 3(1), was chromatographed on a silica gel (Wakogel C300, prepared by Wako pure chemical industries Ltd., 200 g) column with chloroform as an eluent.

(2S,4R)-2-[(Z)-5-Carboxy-1-pentenyl]-1-(4-chlorophenylsulfonyl)-4-(4-chlorophenylsulfonylamino)pyrrolidine (2.50 g) was obtained from the first eluate.

mp: 150.5°–151.5° C.

$^1$H-NMR (CDCl$_3$) δppm: 1.5–1.8 (m, 3H), 2.03 (m, 1H), 2.1–2.2 (m, 2H), 2.41 (t, J=6.5 Hz, 2H), 3.4–3.5 (m, 2H), 3.74 (m, 1H), 4.56 (q, J=7 Hz, 1H), 5.25 (dd, J=10.5, 9 Hz, 1H), 5.48 (dt, J=10.5, 7.5 Hz, 1H), 7.4–7.5 (m, 4H), 7.7–7.8 (m, 4H)

(2S,4R)-2-[(E)-5-Carboxy-1-pentenyl]-1-(4-chlorophenylsulfonyl)-4-(4-chlorophenylsulfonylamino)pyrrolidine (650 mg) was obtained from the second eluate.
mp: 111°–113° C.
¹H-NMR (CDCl₃) δppm: 1.6–1.8 (m, 2H), 1.8–1.9 (m, 2H), 1.9–2.1 (m, 2H), 2.31 (t, J=7.5 Hz, 2H), 3.22 (dd, J=5, 10 Hz, 1H), 3.42 (dd, J=5.5, 10 Hz, 1H), 3.83 (m, 1H), 4.23 (q, J=6 Hz, 1H), 5.17 (dd, J=7.5, 15.5 Hz, 1H), 5.53 (dt, J=15.5, 6.5 Hz, 1H), 7.4–7.5 (m, 4H), 7.65–7.8 (m, 4H)

EXAMPLE 7

The crude (2S,4R)-2-[(E and Z)-5-carboxy-1-pentenyl]-(4-chlorophenylsulfonyl)-4-phenylsulfonylaminopyrrolidine, which was obtained by treating (2S,4R)-2-[(E and Z)-5-carboxy-1-pentenyl]-4-phenylsulfonylaminopyrrolidine trifluoroacetate (29.9 g) according to a similar manner to that of Example 3(1), was chromatographed on a silica gel (Wakogel C300, 700 g) column with chloroform as an eluent. (2S,4R)-2-[(Z)-5-Carboxy-1-pentenyl]-1-(4-chlorophenyl sulfonyl)-4-phenylsulfonylaminopyrrolidine (10.5 g) was obtained from the first eluate.
mp: 121°–123° C.
¹H-NMR (CDCl₃+CD₃OD) δppm: 1.5–1.8 (m, 3H), 1.92 (m, 1H), 2.11 (q, J=6.5 Hz, 2H), 2.33 (t, J=6.5 Hz, 2H), 3.4–3.6 (m, 2H), 3.68 (m, 1H), 4.46 (q, J=8 Hz, 1H), 5.37 (dd, J=10.5, 10 Hz, 1H), 5.45 (dt, J=10.5, 7 Hz, 1H), 7.5–7.7 (m, 5H), 7.7–7.9 (m, 4H)

(2S,4R)-2-[(E)-5-Carboxy-1-pentenyl]-1-(4-chlorophenyl sulfonyl)-4-phenylsulfonylaminopyrrolidine (1.55 g) was obtained from the second eluate.
mp: 155°–156° C.
¹H-NMR (CDCl₃+CD₃OD) δppm: 1.6–1.7 (m, 2H), 1.7–1.8 (m, 2H), 1.9–2.1 (m, 2H), 2.28 (t, J=7.5 Hz, 2H), 3.18 (dd, J=5.5, 10.5 Hz, 1H), 3.47 (m, 1H), 3.76 (m, 1H), 4.28 (q, J=6.5 Hz, 1H), 5.20 (dd, J=8, 15.5 Hz, 1H), 5.54 (dt, J=15.5, 6.5 Hz, 1H), 7.4–7.6 (m, 5H), 7.6–7.7 (m, 2H), 7.75–7.85 (m, 2H)

EXAMPLE 8

To a solution of (2S,4R)-2-[(E and Z)-5-carboxy-1-pentenyl]-1-(4-chlorophenylsulfonyl)-4-(4-chlorophenylsulfonylamino)pyrrolidine (330 mg) in ethyl acetate (15 ml) was added a solution of diazomethane in diethyl ether at 0° C. and the mixture was stirred at the same temperature for 10 minutes. The solvent was evaporated in vacuo and the residue was solidified with n-hexane to give (2S,4R)-1-(4-chlorophenylsulfonyl)-4-(4-chlorophenylsulfonylamino)-2-[(E and Z)-5-methoxycarbonyl-1-pentenyl]pyrrolidine (321 mg) as a white powder.
mp: 87°–89° C.
¹H-NMR (CDCl₃) δppm: 1.5–1.9 (3H, m), 1.9–2.1 (3H, m), 2.2–2.4 (2H, m), 3.43 (2H, m), 3.71 (1H, m), 4.50 (1H, m), 4.96 (1H, d, J=6.5 Hz), 5.2–5.6 (2H, m), 7.4–7.5 (4H, m), 7.6–7.8 (4H, )

EXAMPLE 9

A solution of (2S,4R)-2-[(E and Z)-5-carboxy-1-pentenyl]-1-(4-chlorophenylsulfonyl)-4-(4-chlorophenylsulfonylamino)pyrrolidine (400 mg) in methanol (15 ml) was hydrogenated under medium pressure (2 atm) in the presence of 10% palladium on carbon for 7 hours. After removal of the catalyst, the solvent was evaporated in vacuo and the residue was solidified with diethyl ether to give (2R,4R)-2-(5-carboxypentyl)-1-(4-chlorophenylsulfonyl)-4-(4-chlorophenylsulfonylamino)pyrrolidine (164 mg) as a white powder.
mp: 124°–125° C.
¹H-NMR (CDCl₃) δppm: 1.2–1.4 (4H, m), 1.5–1.7 (3H, m), 1.7–1.9 (3H, m), 2.35 (2H, t, J=7.5 Hz), 3.09 (1H, m), 3.38 (1H, m), 3.6–3.9 (2H, m), 7.4–7.6 (4H, m), 7.7–7.9 (4H, m)

EXAMPLE 10

To a suspension of triphenyl-(4-methoxycarbonylbenzyl)phosphonium chloride (88.49 g) in tetrahydrofuran (500 ml) was added sodium hydride (4.75 g) by portions under an ice bath cooling and the mixture was stirred in an ice bath for 1 hour.
To the resulting yellow suspension was added dropwise a solution of (2S,4R)-1-t-butoxycarbonyl-4-(4-chloro-phenylsulfonylamino)-2-formylpyrrolidine (70.0 g) in tetrahydrofuran (200 ml) under ice bath cooling and the mixture was stirred in an ice bath for 1 hour. To the mixture were added saturated aqueous ammonium chloride (50 ml) and ethyl acetate (1.5 l) and the solution was washed successively with water and brine. The organic layer was dried over magnesium sulfate and the solvent was evaporated in vacuo to give a crude (2S,4R)-1-t-butoxycarbonyl-4-(4-chlorophenylsulfonylamino)-2-[(E and Z)-2-(4-methoxycabonylphenyl)-vinyl]pyrrolidine. The crude product was separated by using a silica gel (1 kg) column with a mixture of n-hexane and ethyl acetate (4:1 - 2:1) as an eluent to give (2S,4R)-1-t-butoxy-carbonyl-4-(4-chlorophenylsulfonylamino)-2-[(Z)-2-(4-methoxycarbonylphenyl)-vinyl]pyrrolidine (Z isomer, 15.98 g, less polar) as a white powder and (2S,4R)-1-t-butoxycarbonyl-4-(4-chlorophenylsulfonylamino)-2-[(E)-2-2-(4-methoxycarbonylphenyl)vinyl]pyrrolidine (E isomer, 21.94 g, more polar) as a white powder.

Z isomer
mp: 178°–179° C.
¹H-NMR (CDCl₃) δppm: 1.29 (9H, s), 1.8–2.3 (2H, m), 3.26 (1H, m), 3.51 (1H, dd, J=6, 11 Hz), 3.89 (1H, m), 3.93 (3H, s), 4.78 (1H, m), 5.10 (1H, m), 5.60 (1H, dd, J=9, 11.5 Hz), 6.48 (1H, d, J=11.5 Hz), 7.2–7.4 (2H, m), 7.48 (2H, d, J=8.5 Hz), 7.82 (2H, d, J=8.5 Hz), 8.02 (2H, d, J=8.5 Hz)

E isomer
mp: 164°–165° C.
¹H-NMR (CDCl₃) δppm: 1.39 (9H, s), 1.9–2.2 (2H, m), 3.24 (1H, dd, J=5, 11 Hz), 3.55 (1H, dd, J=6, 11.5 Hz), 3.91 (3H, s), 3.8–4.0 (1H, m), 4.49 (1H, m), 4.91 (1H, m), 6.12 (1H, dd, J=6.5, 15.5 Hz), 7.37 (2H, d, J=8.5 Hz), 7.50 (2H, d, J=8.5 Hz), 7.82 (2H, d, J=8.5 Hz), 7.97 (2H, d, J=8.5 Hz)

EXAMPLE 11

The following compounds were obtained according to a similar manner to that of Example 10.
(2S,4R)-1-t-Butoxycarbonyl-4-(4-chlorophenylsulfonyl-amino)-2-[(Z)-2-(3-methoxycarbonylphenyl)vinyl]pyrrolidine
mp: 154°–156° C.
¹H-NMR (CDCl₃) δppm: 1.28 (9H, s), 1.8–2.1 (2H, m), 3.30 (1H, dd, J=5, 12 Hz), 3.56 (1H, dd, J=6, 12 Hz), 3.89 (1H, m), 3.93 (3H, s), 4.79 (1H, m), 4.93 (1H, d, J=7 Hz), 5.58 (1H, dd, J=9, 12.5 Hz), 6.48 (1H, d, J=12.5 Hz), 7.3–7.5 (4H, m), 7.83 (2H, d, J=8.5 Hz), 7.92 (2H, m)

2S,4R)-1-t-Butoxycarbonyl-4-(4-chlorophenylsulfonylamino-2-[(E)-2-(3-methoxycarbonylphenyl)vinyl]-pyrrolidine mp: 126°–128° C.

$^1$H-NMR (CDCl$_3$) δppm: 1.40 (9H, s), 1.8–2.1 (2H, m), 3.24 (1H, dd, J=5.5, 11 Hz), 3.57 (1H, dd, J=6, 11 Hz), 3.92 (3H, s), 3.97 (1H, m), 4.49 (1H, m), 4.88 (1H, m), 6.09 (1H, dd, J=6.5, 16 Hz), 6.43 (1H, d, J=16 Hz), 7.49 (1H, t, J=7.5 Hz), 7.4–7.6 (3H, m), 7.33 (2H, d, J=8.5 Hz), 7.92 (1H, d, J=7 Hz), 8.03 (1H, s)

EXAMPLE 12

(1) A solution of (2S,4R)-1-t-butoxycarbonyl-4-(4-chlorophenylsulfonylamino)-2-[(Z)-2-(4-methoxycarbonylphenyl)vinyl]pyrrolidine (15.5 g) in 90% aqueous trifluoroacetic acid (100 ml) was stirred at room temperature for 30 minutes and the solvent was evaporated in vacuo. The residue was suspended in chloroform (200 ml) and the solution was adjusted to pH 8 with saturated aqueous sodium bicarbonate. The organic phase was separated, washed with brine and dried over magnesium sulfate. The solvent was evaporated in vacuo and the residual solid was collected by filtration to give (2S,4R)-4-(4-chlorophenylsulfonylamino-2-[(Z)-2-(4-methoxycarbonylphenyl)vinyl]pyrrolidine (11.9 g) as a white powder.

mp: 189°–190° C.

$^1$H-NMR (CDCl$_3$) δppm: 1.7–2.2 (2H, m), 2.66 (1H, dd, J=4.5, 11.5 Hz), 3.18 (1H, dd, J=6, 11.5 Hz), 3.88 (1H, m), 3.93 (3H, s), 4.08 (1H, m), 5.61 (1H, dd, J=9.5, 11.5 Hz), 6.52 (1H, d, J=11.5 Hz), 7.28 (2H, d, J=8.5 Hz), 7.49 (1H, d, J=8.5 Hz), 7.80 (1H, d, J=8.5 Hz), 8.00 (2H, d, J=8.5 Hz)

The following compounds were obtained according to a similar manner to that of Example 12(1).

(2) (2S,4R)-4-(4-Chlorophenylsulfonylamino)-2-(Z)-2-(3-methoxycarbonylphenyl)vinyl]pyrrolidine $^1$H-NMR (CDCl$_3$) δppm: 1.75 (1H, dd, J=7.5, 14 Hz), 1.91 (1H, m), 2.74 (1H, dd, J=5, 12 Hz), 3.26 (1H, dd, J=6, 12 Hz), 3.90 (1H, m), 3.92 (3H, s), 4.13 (1H, m), 5.62 (1H, dd, J=9.5, 12 Hz), 6.51 (1H, d, J=12 Hz), 7.3–7.5 (5H, m), 7.7–8.0 (3H, m)

(3) (2S,4R)-4-(4-Chlorophenylsulfonylamino)-2-[(E)-(3-methoxycarbonylphenyl)vinyl]pyrrolidine $^1$H-NMR (CDCl$_3$) δppm: 1.8–2.0 (2H, m), 2.93 (1H, dd, J=4.5, 11.5 Hz), 3.32 (1H, dd, J=6, 11.5 Hz), 3.90 (1H, m), 3.93 (3H, s), 4.05 (1H, m), 6.28 (1H, dd, J=7.5, 16.5 Hz), 6.52 (1H, d, J=16.5 Hz), 7.36 (1H, t, J=7.5 Hz), 7.4–7.5 (3H, m), 7.7–7.9 (3H, m), 8.00 (1H, m)

EXAMPLE 13

(1) To a suspension of (2S,4R)-4-(4-chlorophenylsulfonylamino)-2-[(Z)-2-(4-methoxycarbonylphenyl)-vinyl]pyrrolidine (11.5 g) in dichloromethane (200 ml) were added triethylamine (3.80 ml) and 4-chlorobenzenesulfonyl chloride (5.77 g) under ice bath cooling and the mixture was stirred at room temperature for 1 hour. The solution was washed successively with diluted hydrochloric acid, saturated aqueous sodium bicarbonate and brine and dried over magnesium sulfate. The solvent was evaporated in vacuo and the residual solid was collected by filtration to give (2S,4R)-1-(4-chlorophenylsulfonyl)-4-(4-chlorophenylsulfonylamino)-2-[(Z)-2-(4-methoxycarbonylphenyl)-vinyl]pyrrolidine (15.71 g) as a white powder mp: 171°–172° C.

$^1$H-NMR (CDCl$_3$) δppm: 1.8–2.1 (2H, m), 3.30 (1H, dd, J=4, 11 Hz), 3.53 (1H, dd, J=5.5, 11 Hz), 3.81 (1H, m), 3.97 (3H, s), 4.53 (1H, m), 5.58 (1H, dd, J=9, 11.5 Hz), 6.43 (1H, d, J=11.5 Hz), 7.25 (2H, d, J=8.5 Hz), 7.33 (2H, d, J=8.5 Hz), 7.45 (2H, d, J=8.5 Hz), 7.50 (2H, d, J=8.5 Hz), 7.75 (2H, d, J=8.5 Hz), 8.04 (2H, d, J=8.5 Hz)

The following compounds were obtained according to a similar manner to that of Example 13(1).

(2) (2S,4R)-1-(4-Chlorophenylsulfonyl)-4-(4-chlorophenylsulfonylamino)-2-[(Z)-2-(3-methoxycarbonylphenyl)vinyl]pyrrolidine mp: 203°–204° C.

$^1$H-NMR (DMSO-d$_6$) δppm: 1.8–1.9 (2H, m), 3.23 (1H, dd, J=4.5, 11 Hz), 3.50 (1H, dd, J=5.5, 11 Hz), 3.65 (1H, m), 3.89 (3H, s), 4.40 (1H, m), 5.68 (1H dd, J=9, 11.5 Hz), 6.54 (1H, d, J=11.5 Hz), 7.4–8.0 (12H, m)

(3) (2S,4R)-1-(4-Chlorophenylsulfonyl)-4-(4-chlorophenylsulfonylamino)-2-[(E)-2-(3-methoxycarbonylphenyl)vinyl]pyrrolidine mp: 138°–139° C.

$^1$H-NMR (DMSO-d$_6$) δppm: 1.7–1.9 (2H, m), 3.13 (1H, dd, J=5, 9.5 Hz), 3.53 (1H, dd, J=6.5, 9.5 Hz), 3.78 (1H, m), 4.33 (1H, m), 6.23 (1H, dd, J=7.5, 16 Hz), 6.57 (1H, d, J=16 Hz), 7.4–8.0 (12H, m)

EXAMPLE 14

(1) A solution of (2S,4R)-1-(4-chlorophenyl-sulfonyl)-4-(4-chlorophenylsulfonylamino)-2-[(Z)-2-(4methoxycarbonylphenyl)vinyl]pyrrolidine (15.0 g) in a mixture of methanol (100 ml) and 1N aqueous sodium hydroxide (75 ml) was stirred at 50° C. for 4 hours and the volatile solvent was evaporated in vacuo. The residual aqueous solution was adjusted to pH 1 with concentrated hydrochloric acid. The white precipitate was collected by filtration and washed with water to give (2S,4R)-2-[(Z)-2-(4-carboxyphenyl)vinyl]-1-(4-chlorophenylsulfonyl)-4-(4-chlorophenylsulfonylamino)pyrrolidine (14.50 g) as a white powder.

mp: 206°–208° C. (dec.)

$^1$H-NMR (DMSO-d$_6$) δppm: 1.8–2.0 (2H, m), 3.31 (1H, dd, J=3.5, 10.5 Hz), 3.51 (1H, dd, J=5.5, 10.5 Hz), 4.40 (1H, m), 5.68 (1H, dd, J=9.5, 11.5 Hz), 6.54 (1H, d, J=11.5 Hz), 7.32 (2H, d, J=8 Hz), 7.40 (2H, d, J=8 Hz), 7.47 (2H, d, J=8 Hz), 7.67. (2H, d, J=8 Hz), 7.78 (2H, d, J=8 Hz), 7.95 (2H, d, J=8 Hz)

The following compounds were obtained according to a similar manner to that of Example 14(1).

(2) (2S,4R)-2-[(E)-2-(4-Carboxyphenyl)vinyl]-1-(4-chlorophenylsulfonyl)-4-(4-chlorophenylsulfonylamino)pyrrolidine mp: 168°–171° C. (dec.)

$^1$H-NMR (DMSO-d$_6$) δppm: 1.7–1.9 (2H, m), 3.08 (1H, dd, J=6, 11 Hz), 3.46 (1H, m), 3.78 (1H, m), 4.32 (1H, m), 6.30 (1H, dd, J=7, 16 Hz), 6.53 (1H, d, J=16 Hz), 7.47 (2H, d, J=8.5 Hz), 7.6–7.7 (4H, m), 7.7–7.8 (4H, m), 7.88 (2H, d, J=8.5 Hz), 8.00 (1H, d, J=6 Hz)

(3) (2S,4R)-2-[(Z)-2-(3-Carboxyphenyl)vinyl]-1-(4-chlorophenylsulfonyl)-4-(4-chlorophenylsulfonylamino)pyrrolidine mp: 127°–130° C.

$^1$H-NMR (DMSO-d$_6$) δppm: 1.8–1.9 (2H, m), 3.23 (1H, dd, J=4.5, 10.5 Hz), 3.50 (1H, dd, J=5, 10.5 Hz), 3.63 (1H, m), 4.41 (1H, m), 5.67 (1H, dd, J=9.5, 12 Hz), 6.54 (1H, d, J=12 Hz), 7.4–8.0 (12H, m)

(4) (2S,4R)-2-[(E)-2-(3-Carboxyphenyl)vinyl]-1-(4-chlorophenylsulfonyl)-4-(4-chlorophenylsulfonylamino)pyrrolidine
mp: 119°–121° C.

$^1$H-NMR (DMSO-d$_6$) δppm: 1.7–1.9 (2H, m), 3.12 (1H, dd, J=5, 9.5 Hz), 3.50 (1H, dd, J=6.5, 9.5 Hz), 3.79 (1H, m), 4.31 (1H, m), 6.23 (1H, dd, J=7.5, 16 Hz), 6.57 (1H, d, J=16 Hz), 7.4–8.0 (12H, m)

EXAMPLE 15

(1) A mixture of L-lysine hydrate (4.01 g) and (2S,4R)-2-[(Z)-5-carboxy-1-pentenyl]-1-(4-chlorophenyl-sulfonyl)-4-(4-chlorophenylsulfonylamino)pyrrolidine (12.0 g) was dissolved in a mixture of hot water (9 ml) and hot ethanol (170 ml) and the solution was cooled to room temperature. The precipitate (white crystal) was collected by filtration, washed with ethanol and dried in vacuo to give L-lysine salt of (2S,4R)-2-[(Z)-5-carboxy-1-pentenyl]-1-(4-chlorophenylsulfonyl)-4-(4-chlorophenylsulfonylamino)pyrrolidine (13.4 g) as white crystals.
mp: 176°–178° C.

$^1$H-NMR (D$_2$O-NaOD) δppm: 1.2–1.4 (5H, m), 1.5–1.7 (5H, m), 1.98 (2H, m), 2.09 (2H, t, J=7.5 Hz), 2.53 (2H, t, J=7.5 Hz), 2.77 (1H, t, J=8.5 Hz), 3.18 (1H, t, J=7 Hz), 3.31 (1H, m), 3.59 (1H, m), 4.44 (1H, m), 5.1–5.4 (2H, m), 7.4–7.7 (8H, m)

The following compound was obtained according to a similar manner to that of Example 15(1).

(2) L-Arginine salt of (2S,4R)-2-[(Z)-5-carboxy-1-pentenyl]-1-(4-chlorophenylsulfonyl)-4-(4-chlorophenylsulfonylamino)pyrrolidine
mp: 139°–145° C.

$^1$H-NMR (D$_2$O-NaOD) δppm: 1.4–1.7 (8H, m), 1.96 (2H, m), 2.09 (2H, t, J=7.5 Hz), 2.74 (1H, t J=9 Hz), 3.07 (2H, m), 3.20 (1H, m), 3.32 (1H, m), 3.60 (1H, m), 4.42 (1H, m), 5.1–5.4 (2H, m), 7.4–7.7 (8H, m)

Preparation 11

To a solution of (2S,4R)-1-t-butoxycarbonyl-4-(4-chlorophenylsulfonylamino)-2-formylpyrrolidine (5.0 g) in dry tetrahydrofuran (50 ml) was added methylmagnesium bromide (10.8 ml, 3 molar solution in ether) at −78° C. and the solution was stirred at the same temperature for 3 hours. After quenching with saturated aqueous ammonium chloride, the mixture was extracted with ethyl acetate and the organic phase was washed successively with water and brine. After the organic phase was dried over magnesium sulfate, the solvent was evaporated in vacuo to give (2S,4R)-1-t-butoxycarbonyl-4-(4-chlorophenylsulfonylamino)-2-[(R and S)-1-hydroxyethyl]pyrrolidine (5.2 g) as an oil.

$^1$H-NMR (CDCl$_3$) δppm: 1.0–1.1 (3H, m), 1.41 (9H, s), 8–2.0 (2H, m), 3.3–3.4 (2H, m), 3.6–4.0 (3H, m), 5.40 (1H, m), 7.52 (2H, d, J=8.5 Hz), 7.84 (2H, d, J=8.5 Hz)

Preparation 12

To a solution of oxalyl chloride (1.57 ml) in dichloromethane (120 ml) was added dimethyl sulfoxide (1.46 ml) at −78° C. After the mixture was stirred at the same temperature for 10 minutes, (2S,4R)-1-t-butoxycarbonyl-4-(4-chlorophenylsulfonylamino)-2-[(R and S)-1-hydroxyethyl]pyrrolidine (5.20 g) in dichloromethane (15 ml) was added thereto at −78° C. and the mixture was stirred at the same temperature for 15 minutes. To the solution was added triethylamine (6.75 ml) and the resulting mixture was stirred at −78° C. for 1 hour. The solution was washed successively with water and brine and dried over magnesium sulfate. The solvent was evaporated in vacuo and the residue was chromatographed on silica gel column with a mixture of n-hexane and ethyl acetate (2:1) as an eluent to give (2S,4R)-1-t-butoxycarbonyl-4-(4-chlorophenylsulfonylamino)-2-acetylpyrrolidine (3.19 g).

$^1$H-NMR (CDCl$_3$) δppm: 1.40 (9H, s), 1.9–2.1 (2H, m), 2.15 (3H, s), 2.31 (1H, m), 3.32 (1H, m), 3.57 (1H, m), 3.84 (1H, broad), 4.42 (1H, m), 5.45 (1/3H, d, J=7 Hz), 5.59 (2/3H, d, J=7 Hz), 7.53 (2H, d, J=8.5 Hz), 7.82 (2H, d, J=8.5 Hz)

Preparation 13

A solution of (2S,4R)-1-t-butoxycarbonyl-4-(4-chlorophenylsulfonylamino)-2-methoxycarbonylpyrrolidine (20 g) in 90% aqueous trifluoroacetic acid was stirred at room temperature for 30 minutes and the solvent was evaporated in vacuo. The residue was dissolved in a mixture of chloroform and methanol (500 ml, 3:1) and the solution was washed successively with saturated aqueous sodium bicarbonate and brine. The organic layer was dried over magnesium sulfate and the solvent was evaporated in vacuo. The residue was solidified with ether to give (2S,4R)-4-(4-chlorophenylsulfonylamino)-2-methoxycarbonylpyrrolidine (10.7 g).

$^1$H-NMR (CDCl$_3$) δppm: 2.07 (1H, d, J=8 Hz), 2.10 (1H, d, J=8 Hz), 2.74 (1H, dd, J=3, 11 Hz), 3.09 (1H, dd, J=5.5, 11 Hz), 3.72 (3H, s), 3.8–3.9 (2H, m), 7.48 (2H, d, J=8.5 Hz), 7.82 (2H, d, J=8.5 Hz)

Preparation 14

To a solution of (2S,4R)-4-(4-chlorophenyl-sulfonylamino)-2-methoxycarbonylpyrrolidine (10.0 g) in dichloromethane (200 ml) were added triethylamine (4.8 ml) and 4-chlorobenzenesulfonyl chloride (6.62 g) in an ice bath and the mixture was stirred in an ice bath for 3 hours. The resulting solution was washed successively with diluted hydrochloric acid, saturated aqueous sodium bicarbonate and brine and dried over magnesium sulfate. The solvent was evaporated in vacuo to give (2S,4R)-1-(4-chlorophenylsulfonyl)-4-(4-chlorophenylsulfonylamino)-2-methoxycarbonylpyrrolidine (11.5 g).

$^1$H-NMR (CDCl$_3$) δppm: 2.14 (2H, t, J=7 Hz), 3.22 (1H, dd, J=4.5, 10 Hz), 3.45 (1H, dd, J=5, 10 Hz), 3.69 (3H, s), 3.93 (1H, m), 4.47 (1H, t, J=7 Hz), 7.45–7.55 (4H, m), 7.7–7.8 (4H, m)

Preparation 15

The following compounds were obtained according to a similar manner to that of Preparation 7(1).

(1) (2S,4R)-1-t-Butoxycarbonyl-4-(4-methylphenylsulfonylamine-2-methoxycarbonylpyrrolidine $^1$H-NMR (CDCl$_3$) δppm: 1.40 (9H, s), 2.1–2.3 (2H, m), 2.45 (3H, s), 3.19 (1H, m), 3.60 (1H, dd, J=6, 11 Hz), 3.71 (3H, s), 3.94 (1H, m), 4.30 (1H, m), 5.20 (1H, m), 7.34 (2H, d, J=8 Hz), 7.77 (2H, d, J=8 Hz)

(2) (2S,4R)-1-t-Butoxycarbonyl-2-methoxycarbonyl-4-(4-methoxyphenylsulfonylamino)pyrrolidine $^1$H-NMR (CDCl$_3$) δppm: 1.48 (9H, s), 2.1–2.3 (2H, m), 3.18 (1H, m), 3.59 (1H, dd, J=6, 11 Hz), 3.70 (3H, s), 3.88 (3H, s), 3.90 (1H, m), 4.28 (1H, m), 5.40 (1H, m), 6.98 (2H, d, J=8 Hz), 7.80 (1H, d, J=8 Hz)

(3) (2S,4R)-1-t-Butoxycarbonyl-2-methoxycarbonyl-4(4-trifluoromethylphenylsulfonylamino)pyrrolidine $^1$H-NMR (CDCl$_3$) δppm: 1.39 (9H, s), 2.0–2.2 (2H, m), 2.30 (1H, m), 3.2–3.4 (1H, m), 3.73 (3H, s), 3.98 (1H, m), 4.33 (1H, m), 7.82 (2H, d, J=8 Hz), 8.04 (2H, d, J=8.0 Hz)

Preparation 16

The following compounds were obtained according to a similar manner to that of Preparation 8(1).

(1) (2S,4R)-1-(4-Chlorophenylsulfonyl)-4-(4-chlorophenylsulfonylamino)-2-formylpyrrolidine (2) (2S,4R)-1-t-Butoxycarbonyl-2-formyl-4-methylphenylsulfonylamino)pyrrolidine ¹H-NMR (CDCl₃) δppm: 1.40 (9H, s), 2.13 (1H, m), 2.47 (3H, s), 3.32 (1H, m), 3.57 (1H, m), 3.82 (1H, m), 4.25 (1H, m), 5.10 (1H, m), 7.34 (2H, d, J=8 Hz), 7.75 (2H, d, J=8 Hz), 9.50 (1H, broad)

(3) (2S,4R)-1-t-Butoxycarbonyl-2-formyl-4-(4-methoxyphenylsulfonylamino)pyrrolidine ¹H-NMR (CDCl₃) δppm: 1.42 (9H, s), 1.88 (1H, m), 2.12 (1H, m), 3.15 (1H, m), 3.7–4.0 (2H, m), 3.88 (3H, s), 4.93 (1H, m), 5.38 (1H, m), 7.02 (2H, d, J=8 Hz), 7.25–7.35 (2H, m), 9.44 (1H, broad)

(4) (2S,4R)-1-t-Butoxycarbonyl-2-formyl-4-(4-trifluoromethylphenylsulfonylamino)pyrrolidine

EXAMPLE 16

A mixture of (2S,4R)-1-t-butoxycarbonyl-4-(4-chlorophenylsulfonylamino)-2-formylpyrrolidine (1.00 g) and ethoxycarbonylmethylenetriphenylphosphorane (1.50 g) in dichloromethane (20 ml) was stirred at room temperature for 2 hours and the solvent was evaporated in vacuo. The residual oil was chromatographed on silica gel column with a mixture of n-hexane and ethyl acetate (2:1) as an eluent to give (2S,4R)-1-t-butoxycarbonyl-(4-chlorophenylsulfonylamino)-2-[(E)-2-ethoxycarbonylvinyl]pyrrolidine (1.15 g) as an oil.

¹H-NMR (CDCl₃) δppm: 1.30 (3H, t, J=7.5 Hz), 1.38 (9H, s), 1.98 (1H, m), 2.15 (1H, m), 3.22 (1H, m), 3.53 (1H, m), 3.85 (1H, m), 4.20 (2H, q, J=7.5 Hz), 4.46 (1H, m), 4.92 (1H, m), 5.80 (1H, d, J=15.5 Hz), 6.73 (1H, dd, J=6, 15.5 Hz), 7.52 (2H, d, J=8.5 Hz), 7.81 (2H, d, J=8.5 Hz)

EXAMPLE 17

A solution of (2S,4R)-1-t-butoxycarbonyl-2-(E and Z)-5-carboxy-1-pentenyl]-4-(4-chlorophenylsulfonylamino)pyrrolidine (1.14 g) in methanol (20 ml) saturated with hydrogen chloride was stirred at room temperature overnight and the solvent was evaporated in vacuo. The residue was dissolved in chloroform and the solution was washed successively with saturated aqueous sodium bicarbonate and brine. The solution was dried over magnesium sulfate and the solvent was evaporated in vacuo to give (2S,4R)-4-(4-chlorophenylsulfonylamino)-2-[(E and Z)-5-methoxycarbonyl-1-pentenyl]pyrrolidine (908 mg) as an oil.

¹H-NMR (CDCl₃) δppm: 1.6–1.9 (4H, m), 2.07 (2H, m), 2.29 (2H, m), 2.73 (1H, m), 3.22 (1H, m), 3.66 (3×1/3H, s), 3.68 (3×2/3H,s) 30, 3.85 (1H, m), 4.03 (1H, m), 5.2–5.6 (2H, m), 7.4–7.6((2H, m), 7.8–7.9 (2H, m)

EXAMPLE 18

A solution of (2S,4R)-1-t-butoxycarbonyl-4-(4-chlorophenylsulfonylamino)-2-[(E)-2-ethoxycarbonylvinyl]pyrrolidine (1.10 g) in 90% aqueous trifluoroacetic acid (10 ml) was stirred at room temperature for 1 hour and the solvent was evaporated in vacuo. The residue was dissolved in ethyl acetate and the solution was washed successively with saturated aqueous sodium bicarbonate and brine. The organic solution was dried over magnesium sulfate and evaporated in vacuo to give (2S,4R)-4-(4-chlorophenylsulfonylamino)-2-[(E)-2-ethoxycarbonylvinyl]pyrrolidine (596 mg) as an oil.

EXAMPLE 19

The following compounds were obtained according to a similar manner to that of Example 3(1).

(1) (2S,4R)-4-(4-Chlorophenylsulfonylamino)-2-[-(E and Z)-5-methoxycarbonyl-1-pentenyl]-1-(2-thienylsulfonyl)pyrrolidine ¹H-NMR (CDCl₃) δppm: 1.6–1.9 (4H, m), 1.9–2.2 (2H, m), 2.33 (2H, m), 3.37 (1H, dd, J=3, 12.5 Hz), 3.59 (1H, dd, J=5, 12.5 Hz), 3.67 (3×1/3H, s), 3.69 (3×2/3H, s), 3.79 (1H, m), 4.22 (1×1/3H, q, J=7 Hz), 4.52 (1×2/3H, q, J=7 Hz), 4.62 (1×1/3H, d, J=7 Hz), 4.78 (1×2/3H, d, J=6 Hz), 5.3–5.7 (2H, m), 7.1–7.2 (1H, m), 7.5–7.7 (4H, m), 7.7–7.8 (2H, m)

(2) (2S,4R)-1-(4-Chlorophenylsulfonyl)-4-(4-chlorophenylsulfonylamino)-2-[(E)-2-ethoxycarbonylvinyl]pyrrolidine ¹H-NMR (CDCl₁) δppm: 1.28 (3H, t, J=7 Hz), 1.9–2.1 (2H, m), 3.23 (1H, dd, J=5, 11 Hz), 3.50 (1H, dd, J=5.5, 11 Hz), 3.85 (1H, m), 4.18 (1H, q, J=7 Hz), 4.43 (1H, q, J=6 Hz), 4.85 (1H, d, J=9.5 Hz), 5.90 (1H, d, J=15 Hz), 6.62 (1H, dd, J=6, 15 Hz), 7.51 (2H, d, J=8.5 Hz), 7.52 (2H, d, J=8.5 Hz), 7.73 (2H, d, J=8.5 Hz), 7.79 (2H, d, J=8.5 Hz)

(3) (2S,4R)-2-[(E and Z)-5-Carboxy-1-methyl-1-pentenyl]-(4-chlorophenylsulfonyl)-4-(4-chlorophenylsulfonylamino)pyrrolidine mp: 106°–110° C.

¹H-NMR (CDCl₃) δppm: 1.59 (3H, s), 1.6–1.8 (2H, m), 1.84 (1H, m), 2.0–2.2 (3H, m), 2.38 (2H, t, J=7.0 Hz), 3.18 (1H, m), 3.42 (1H, m), 3.74 (1H, m), 4.45 (1H, t, J=7.0 Hz), 5.22 (1H, m), 5.40 (1H, d, J=7.0 Hz), 7.4–7.5 (4H, m), 7.65–7.8 (4H, m)

EXAMPLE 20

(1) To a solution of (4-carboxy-4-methylpentyl)triphenylphosphonium bromide (3.83 g) in dimethyl sulfoxide (21 ml) was added sodium methylsulfinylmethide [19.5 m mol, prepared from sodium hydride (468 mg) and dimethyl sulfoxide (17 ml)]and the solution was stirred at room temperature for 30 minutes. To the resulting solution was added (2S,4R)-1-t-butoxycarbonyl-4-(4-chlorophenylsulfonylamino)-2-formylpyrrolidine (1.0 g) in dimethyl sulfoxide (3.0 ml) and the mixture was stirred at room temperature for 1 hour. After addition of water (50 ml), the solution was washed with ethyl acetate and the aqueous layer was adjusted to pH 1 with 1N hydrochloric acid. The aqueous solution was extracted with ethyl acetate and the organic phase was washed successively with water and brine. The solution was dried over magnesium sulfate and the solvent was evaporated in vacuo to give (2S,4R)-1-t-butoxycarbonyl-2-[(E and Z)-5-carboxy-5-methyl-1-hexenyl]-4-(4-chlorophenylsulfonylamino)pyrrolidine as an oil.

The following compounds were obtained according to a similar manner to that of Example 20(1).

(2) (2S,4R)-1-t-Butoxycarbonyl-2-[(E and Z)-6-carboxy-hexenyl]-4-(4-chlorophenylsulfonylamino)pyrrolidine ¹H-NMR (CDCl₁) δppm: 1.40 (9H, s), 1.4–1.5 (2H, m), 1.6–1.8 (3H, m), 1.9–2.1 (3H, m), 2.3–2.4 (2H, m), 3.39 (1H, m), 3.86 (1H, m), 4.58 (1H, m), 5.3–5.5 (2H, m), 7.50 (2H, m), 7.81 (2H, m)

(3) (2S,4R)-1-t-Butoxycarbonyl-2-[(E and Z)-5-carboxy-1-hexenyl]-4-(4-chlorophenylsulfonylamin)pyrrolidine (4) (2S,4R)-1-t-Butoxycarbonyl-2-[(E and Z)-5-carboxy-1-methyl-1-pentenyl]-4-(4-chlorophenylsulfonylamino)pyrrolidine ¹H-NMR (CDCl₃) δppm: 1.34 (9H, s), 1.5 (3H, m), 1.6–1.8 (3H, m), 2.0–2.2 (3H, m), 2.3–2.4 (2H, m), 3.39 (1H, m), 3.78 (2H, m), 4.50 (1H, m), 5.1–5.3 (1H, m), 7.49 (2H, d, J=8.5 Hz), 7.83 (2H, d, J=8.5 Hz)

(5) (2S,4R)-1-t-Butoxycarbonyl-2- (E and Z)-5-carboxy-1-pentenyl]-4-(4-methylphenylsulfonylamino)pyrrolidine (6) (2S,4R)-1-t-Butoxycarbonyl-2-[(E and Z)-5-carboxy-1-pentenyl]-4-(4-methoxyphenylsulfonylamino)pyrrolidine (7) (2S,4R)-1-t-Butoxycarbonyl-2-[(E and Z)-5-carboxy-1-pentenyl]-4-(4-trifluoromethylphenylsulfonylamino)pyrrolidine

EXAMPLE 21

(1) (2S,4R)-1-t-Butoxycarbonyl-2-[(E and Z)-5-carboxy-5-methyl-1-hexenyl]-4-(4-chlorophenylsulfonylamino)pyrrolidine obtained in Example 20(1) was dissolved in 75% aqueous trifluoroacetic acid (8 ml) and the solution was stirred at room temperature for 1 hour. The solvent was evaporated in vacuo to give (2S,4R)-2-[(E and Z)-5-carboxy-5-methyl-1-hexenyl]-4-(4-chlorophenylsulfonylamino)pyrrolidine trifluoroacetate as an oil.

The following compounds were obtained according to a similar manner to that of Example 21(1).

(2) (2S,4R)-2-[(E and Z)-6-Carboxy-1-hexenyl]-4-(4-chlorophenylsulfonylamino)pyrrolidine trifluoroacetate (3) (2S,4R)-2-[(E and Z)-5-Carboxy-1-hexenyl]-4-(4-chlorophenylsulfonylamino)pyrrolidine trifluoroacetate (4) 2S,4R)-2- (E and Z)-5-Carboxy-1-methyl-1-pentenyl]-4-(4-chlorophenylsulfonylamino)pyrrolidine trifluoroacetate (5) (2S,4R)-2-[(E and Z)-5-Carboxy-1-pentenyl]-4-(4-methylphenylsulfonylamino)pyrrolidine trifluoroacetate (6) (2S,4R)-2-[(E and Z)-5-Carboxy-1-pentenyl]-4-(4-methoxyphenylsulfonylamino)pyrrolidine trifluoroacetate (7) (2S,4R)-2-[(E and Z)-5-Carboxy-1-pentenyl]-4-(4-trifluoromethylphenylsulfonylamino)pyrrolidine trifluoroacetate

EXAMPLE 22

(1) To a mixture of (2S,4R)-2-[(E and Z)-5-carboxy-5-methyl-1-hexenyl]-4-(4-chlorophenylsulfonylamino)pyrrolidine trifluoroacetate obtained in Example 21(1) and dichloromethane (13 ml) were added triethylamine (2.0 ml) and 4-chlorobenzenesulfonyl chloride (380 mg) in an ice bath and the mixture was stirred at the same temperature for 1 hour. After addition of 1N hydrochloric acid, the solution was extracted with dichloromethane and the organic layer was washed successively with water and brine, dried over magnesium sulfate. The solvent was evaporated in vacuo and the residue was chromatographed on silica gel (Wako gel C-300) with chloroform as an eluent to give (2S,4R)-2-[(Z)-5-carboxy-5-methyl-1-hexenyl]-1-(4-chlorophenylsulfonyl)-4-(4-chlorophenylsulfonylamino)pyrrolidine
mp: 159°–160° C.

¹H-NMR (CD₃OD) δppm: 1.20 (3H, s), 1.22 (3H, s), 1.5–1.8 (5H, m), 2.0–2.2 (2H, m), 3.43 (1H, m), 3.64 (1H, m), 4.43 (1H, q, J=8 Hz), 5.2–5.4 (2H, m), 7.57 (2H, d, J=7.5 Hz), 7.61 (2H, d, J=7.5 Hz), 7.77 (2H, d, J=7.5 Hz), 7.78 (2H, d J=7.5 Hz)

The following compounds were obtained according to a similar manner to that of Example 22(1).

(2) (2S,4R)-2-[(Z)-6-Carboxy-1-hexenyl]-1-(4-chlorophenylsulfonyl)-4-(4-chlorophenylsulfonylamino)pyrrolidine
mp: 112°–114° C.

¹H-NMR (CDCl₃+CD₃OD) δppm: 1.3–1.5 (2H, m), 1.5–1.8 (4H, m), 1.93 (1H, m), 2.09 (2H, q, J=7.5 Hz), 2.32 (2H, t, J=7.5 Hz), 3.41 (1H, m), 3.74 (1H, m), 4.52 (1H, q, J=8.5 Hz), 5.50 (1H, dd, J=8.5, 10 Hz), 5.42 (dt, J=7.5, 10 Hz), 7.50 (4H, d, J=8 Hz), 7.71 (2H, d, J=8 Hz), 7.78 (2H, d, J=8 Hz)

(3) (2S,4R)-2-[(Z)-5-Carboxy-1-hexenyl]-1-(4-chlorophenylsulfonyl)-4-(4-chlorophenylsulfonylamino)pyrrolidine
mp 159°–160° C. ¹H-NMR (CDCl₃+CD₃OD) δppm: 1.12 (3×1/3H, d, J=6.5 Hz), 1.13 (3×2/3H, d, J=6.5 Hz), 1.3–1.5 (2H, m), 1.6–1.8 (2H, m), 1.87 (1H, m), 1.9–2.1 (2H, m), 2.34 (1H, m), 3.3–3.5 (2H, m), 4.42 (1H, q, J=8 Hz), 5.13 (1H, m), 5.34 (1H, m), 7.35–7.45 (4H, m), 7.6–7.7 (4H, m)

(4) (2S,4R)-2-[(Z)-5-Carboxy-1-pentenyl]-1-(4-chlorophenylsulfonyl)-4-(4-methylphenylsulfonylamino)pyrrolidine
mp: 98°–101° C.

¹H-NMR (CDCl₃) δppm: 1.5–1.8 (5H, m), 1.98 (1H, m), 2.1–2.2 (2H, m), 2.43 (3H, s), 3.4–3.5 (2H, m), 3.69 (1H, m), 4.52 (1H, q, J=7.5 Hz), 5.2–5.5 (3H, m), 7.32 (2H, d, J=8 Hz), 7.50 (2H, d, J=8 Hz), 7.68 (2H, d, J=8 Hz), 7.75 (2H, d, J=8 Hz)

(5) (2S,4R)-2-[(Z)-5-Carboxy-1-pentenyl]-1-(4-chlorophenylsulfonyl)-4-(4-methoxyphenylsulfonylamino)pyrrolidine
mp: 90° C.

¹H-NMR (CDCl₃) δppm: 1.5–1.8 (3H, m), 2.02 (1H, m), 2.17 (2H, q, J=7.5 Hz), 2.49 (2H, t, J=6.5 Hz), 3.4–3.5 (2H, m), 3.66 (1H, m), 3.88 (3H, s) 4.50 (1H, q, J=7 Hz), 5.2–5.5 (3H, m), 6.98 (2H, d, J=8 Hz), 7.50 (2H, d, J=8 Hz), 7.75 (4H, d, J=8 Hz)

(6) (2S,4R)-2-[(Z)-5-Carboxy-1-pentenyl]-1-(4-chlorophenylsulfonyl)-4-(4-trifluoromethylphenylsulfonylamino)pyrrolidine
mp: 140°–141° C.

¹H-NMR (CDCl₃) δppm: 1.5–1.8 (3H, m), 2.05 (1H, m), 2.18 (2H, q, J=7.5 Hz), 2.40 (2H, t, J=6.5 Hz), 3.41 (dd, J=4.5, 11 Hz), 3.53 (1H, dd, J=3, 11 Hz), 3.79 (1H, m), 4.65 (1H, q, J=7 Hz), 5.22 (1H, dd, J=11, 10 Hz), 5.44 (1H, dt, J=11, 7.5 Hz), 5.78 (1H, d, J=6.5 Hz), 7.45 (2H, d, J=8 Hz), 7.72 (2H, d, J=8 Hz), 7.89 (2H, d, J=8 Hz), 7.98 (2H, d, J=8 Hz)

EXAMPLE 23

Thionyl chloride (0.32 ml) was added to methanol (20 ml) at −78° C. and the solution was stirred at the same temperature for 30 minutes. To the solution was added (2S,4R)-2-[(Z)-5-carboxy-1-pentenyl]-1-(4-chlorophenylsulfonyl)-4-(4-chlorophenylsulfonylamino)pyrrolidine (2.0 g) and the mixture was stirred at room temperature for 2 hours. After removal of the solvent by evaporation in vacuo, the residue was dissolved in chloroform and washed successively with saturated aqueous sodium bicarbonate and brine. The organic layer was dried over magnesium sulfate and the solvent was evaporated in vacuo. The residue was solidified with ether to give (2S,4R)-1-(4-chlorophenylsulfonyl)-4-(4-chlorophenylsulfonylamino)-2-[(Z)-methoxycarbonyl-1-pentenyl]pyrrolidine (2.0 g).

mp: 95°–96° C.

¹H-(CDCl₃) δppm: 1.5–1.9 (3H, m), 1.95–2.15 (3H, m), 2.32 (2H, t, J=7.5 Hz), 3.40–3.45 (2H, m), 3.67 (3H, s), 3.81 (1H, m), 4.48 (1H, q, J=8 Hz), 4.94 (1H, d, J=7.5 Hz), 5.23 (1H, t, J=10.5 Hz), 5.46 (1H, m), 7.4–7.5 (4H, m), 7.6–7.8 (4H, m)

EXAMPLE 24

The following compounds were obtained according to a similar manner to that of Example 9.

(1) (2R,4R)-2-[2-(4-Carboxyphenyl)ethyl]-1-(4-chlorophenylsulfonyl)-4-(4-chlorophenylsulfonylamino)pyrrolidine mp: 180°–182° C. (dec.)

¹H-NMR (CDCl₃) δppm: 1.6–1.9 (2H, m), 2.21 (1H m), 2.5–2.8 (2H, m), 3.08 (1H, dd, J=6, 11 Hz), 3.4–3.8 (4H, m), 7.18 (2H, d, J=8.5 Hz), 7.4–7.5 (4H, m), 7.61 (2H, d, J=8.5 Hz), 7.73 (2H, d, J=8.5 Hz), 7.97 (2H, d, J=8.5 Hz)

(2) (2R,4R)-2-[2-(3-Carboxyphenyl)ethyl]-1-(4-chlorophenylsulfonyl)-4-(4-chlorophenylsulfonylamino)pyrrolidine mp: 206°–207° C.

¹H-NMR (DMSO-d ) δppm: 1.54 (1H, m), 1.7–1.85 (2H, m), 2.05 (1H, m), 2.55–2.7 (2H, m), 3.02 (1H, m), 3.3–3.7 (3H, m), 7.45 (2H, d J=8 Hz), 7.65–7.85 (6H, m), 12.93 (1H, broad)

EXAMPLE 25

(1) A solution of (2S,4R)-4-(4-chlorophenylsulfonylamino)-2-[(E and Z)-5-methoxycarbonyl-1-pentenyl]-1(2-thienylsulfonyl)pyrrolidine (890 mg) in a mixture of methanol and 1N aqueous sodium hydroxide (2 ml) was stirred at room temperature overnight. The solution was adjusted to pH 2 with 1N hydrochloric acid and the mixture was extracted with chloroform. The organic solution was washed with brine and dried over magnesium sulfate. The solvent was evaporated in vacuo and the residue was chromatographed on silica gel (Wako gel C-300) with chloroform as an eluent to give (2S,4R)-2-(Z)-5-carboxy-1-pentenyl]-4-(4-chlorophenylsulfonylamino)-1-(2-thienylsulfonyl)pyrrolidine (242 mg) as a white powder.

mp: 115°–116° C.

¹H-NMR (CDCl₃+CD₃OD) δppm: 1.5–2.0 (4H, m), 2.15 (2H, q, J=7 Hz), 2.33 (2H, t, J=7.5 Hz), 3.3–3.6 (2H, m), 3.68 (1H, m), 4.52 (1H, q, J=8 Hz), 5.3–5.5 (2H, m), 7.17 (1H, dd, J=3, 5 Hz), 7.50 (2H, d, J=8.5 Hz), 7.60 (1H, m), 7.66 (1H, m), 7.75 (2H, d, J=8.5 Hz)

The following compounds were obtained according to a similar manner to that of Example 25(2).

(2) (2S,4R)-2-[(E)-2-Carboxyvinyl]-1-(4-chlorophenylsulfonyl)-4-(4-chlorophenylsulfonylamino)pyrrolidine mp: 76°–81° C.

¹H-NMR (CDCl₃+CD₃OD) δppm: 1.88 (2H, t, J=6 Hz), 3.23 (1H, dd, J=5.5, 11 Hz), 3.51 (1H, dd, J=6, 11 Hz), 3.74 (1H, m), 4.38 (1H, q, J=6.5 Hz), 5.91 (1H, d, J=16 Hz), 6.65 (1H, dd, J=6.5, 16 Hz), 7.45–7.55 (4H, m), 7.7–7.8 (4H, m)

(3) (2S,4R)-2-[(Z)-5-Carboxy-1-pentenyl]-1-(4-chlorophenylsulfonyl)-4-[N-(4-chlorophenylsulfonyl)N-methylamino]pyrrolidine mp: 90°–92° C.

¹H-NMR (CDCl₃) δppm: 1.6–1.8 (3H, m), 2.02 (1H, dt, J=8.5, 12.5 Hz), 2.18 (2H, q, J=7.5 Hz), 2.37 (2H, t, J=8 Hz), 2.68 (3H, s), 3.13 (1H, dd, J=7.5, 10 Hz), 3.37 (1H, dd, J=7.5, 10 Hz), 4.5–4.7 (2H, m), 5.22 (1H, t, J=10.5 Hz), 5.40 (1H, dt, J=7.5, 10.5 Hz), 7.45–7.55 (4H, m), 7.65–7.75 (4H, m)

EXAMPLE 26

(1) To a solution of (2S,4R)-2-[(Z)-5-carboxy-1-pentenyl]-1-(4-chlorophenylsulfonyl)-4-(4-chlorophenylsulfonylamino)pyrrolidine (547 mg), benzenesulfonamide (157 mg) and 4-dimethylaminopyridine (122 mg) in dichloromethane (10 ml) was added N,N'-dicyclohexylcarbodiimide (206 mg) and the mixture was stirred at room temperature overnight. After removal of the insoluble material by filtration, the filtrate was evaporated in vacuo and the residue was chromatographed on silica gel column with a mixture of chloroform and methanol (40:1) as an eluent to give (2S,4R)-1-(4-chlorophenylsulfonyl)-4-(4-chlorophenylsulfonylamino)-2-[(Z)-5-{N-(phenylsulfonyl)carbamoyl}-1-pentenyl]pyrrolidine (478 mg).

mp: 150°–152° C.

¹H-NMR (CDCl₃+CD₃OD) δppm: 1.55–1.75 (3H, m), 1.88 (1H, m), 2.09 (2H, q, J=7.5 Hz), 2.27 (2H, q, J=7.5 Hz), 3.36 (1H, m), 3.50 (1H, m), 3.64 (1H, m), 4.45 (1H, q, J=7.5 Hz), 5.2–5.4 (2H, m), 7.45–7.65 (7H, m), 7.7–7.8 (4H, m), 8.0–8.1 (2H, m)

The following compound was obtained according to a similar manner to that of Example 26(1).

(2) (2S,4R)-1-(4-Chlorophenylsulfonyl)-4-(4-chlorophenylsulfonylamino)-2-[(Z)-5-{N-(methylsulfonyl)carbamoyl}-1-pentenyl]pyrrolidine mp: 123°–124° C.

¹H-NMR (CDCl₃+CD₃OD) δppm: 1.6–1.8 (3H, m), 1.95 (1H, m), 2.17 (2H, q, J=7.5 Hz), 2.33 (2H, t, J=7.5 Hz), 3.27 (3H, s), 3.4–3.55 (2H, m), 3.68 (1H, m), 4.52 (1H, q, J=7.5 Hz), 5.2–5.5 (2H, m), 7.5–7.6 (4H, m), 7.85–7.95 (4H, m)

EXAMPLE 27

A mixture of (2S,4R)-2-[(Z)-5-carboxy-1-pentenyl]-1-(4-chlorophenylsulfonyl)-4-(4-chlorophenylsulfonylamino)pyrrolidine (500 mg), N-hydroxysuccinimide (105 mg) and N,N'-dicyclohexylcarbodiimide (188 mg) in tetrahydrofuran (20 ml) was stirred at room temperature overnight. After filtration, the filtrate was evaporated in vacuo to give active ester as an oil.

A mixture of active ester and 28% ammonium hydroxide (1.0 ml) in tetrahydrofuran (10 ml) was stirred at room temperature for 30 minutes and a mixture of chloroform (30 ml) and methanol (10 ml) was added to the solution. The solution was washed successively with water and brine and dried over magnesium sulfate. The solvent was evaporated in vacuo and the residue was solidified with ether to give (2S,4R)-2-[(Z)-5-carbamoyl-1-pentenyl]-1-(4-chlorophenylsulfonyl)-4-(4-chlorophenylsulfonylamino)pyrrolidine (447 mg).

mp: 142°–143° C.

¹H-NMR (CDClhd 3) δppm: 1.6–1.8 (3H, m), 1.93 (1H, m), 2.13 (2H, q, J=7.5 Hz), 2.25 (2H, t, J=7.5 Hz), 3.4–3.55 (2H, m), 3.62 (1H, m), 4.53 (1H, q, J=8 Hz), 5.30 (1H, t, J=10 Hz), 5.48 (1H, dt, J=7.5, 10 Hz), 7.45–7.55 (4H, m), 7.75–7.85 (4H, m)

EXAMPLE 28

To a solution of (2S,4R)-1-(4-chlorophenylsulfonyl)-4-(4-chlorophenylsulfonylamino)-2-[(Z)-5-methoxycarbonyl-1-pentenyl]pyrrolidine 500 mg) in dry tetrahydrofuran (20 ml) was added lithium aluminum hydride (34 mg) under ice bath cooling. After the mixture was stirred in an ice bath for 30 minutes, aqueous tetrahydrofuran was added thereto and the mixture was filtered through Celite. The filtrate was washed successively with water and brine and dried over magnesium sulfate. The solvent was evaporated in vacuo and the residue was solidified with ether to give (2S,4R)-1-(4-chlorophenylsulfonyl)-4-(4-chlorophenylsulfonylamino)-2-[(Z)-6-hydroxy-1-hexenyl]pyrrolidine (350 mg).

mp: 108°–109° C.

$^1$H-NMR (CDCl$_3$) δppm: 1.4–1.6 (4H, m), 1.77 (1H, m), 2.0–2.2 (3H, m), 3.4 (2H, d, J=4 Hz), 3.67 (2H, t, J=6.5 Hz), 3.85 (1H, m), 4.66 (1H, q, J=7.5 Hz), 5.13 (1H, t, J=11 Hz), 5.42 (1H, dt, J=11, 7.5 Hz), 5.76 (1H, d, J=7.5 Hz), 7.50 (2H, d, J=8.5 Hz), 7.52 (2H, d, J=8.5 Hz), 7.73 (2H, d, J=8.5 Hz), 7.80 (2H, d, J=8.5 Hz)

EXAMPLE 29

A solution of (2S,4R)-2-[(Z)-5-carboxy-1-pentenyl]-1-(4-chlorophenylsulfonyl)-4-(4-chlorophenylsulfonylamino)pyrrolidine (839 mg) in thionyl chloride (5.0 ml) was stirred at 0° C. for 1 hour and the solution was evaporated in vacuo to give acid chloride as an oil. To a mixture of mercaptopyridine N-oxide (242 mg) and 4-dimethylaminopyridine (19 mg) in bromotrichloromethane (15 ml) was added acid chloride in bromotrichloromethane (9 ml) under reflux and the solution was refluxed for 2 hours. The solvent was evaporated in vacuo and the residual oil was chromatographed on silica gel with chloroform as an eluent to give (2S,4R)-2-[(Z)-5-bromo-1-pentenyl]-1-(4-chlorophenylsulfonyl)-4-(4-chlorophenylsulfonylamino)pyrrolidine (555 mg) as an oil.

$^1$H-NMR (CDCl$_3$) δppm: 1.7–2.0 (4H, m), 2.22 (2H, q, J=7 Hz), 3.3–3.5 (4H, m), 3.83 (1H, m), 4.61 (1H, q, J=8.5 Hz), 5.15–5.45 (3H, m), 7.4–7.5 (4H, m), 7.7–7.8 (4H, m)

EXAMPLE 30

A mixture of (2S,4R)-2-[(Z)-5-bromo-1-pentenyl]-1-(4-chlorophenylsulfonyl)-4-(4-chlorophenylsulfonylamino)pyrrolidine (527 mg) and sodium sulfite (630 mg) in water (2.3 ml) was refluxed for 9 hours and the solution was subjected to a column of Diaion HP 20. The column was washed with water and the product was eluted with methanol. The object fractions were evaporated and lyophilized to give sodium salt of (2S,4R)-1-(4-chlorophenylsulfonyl)-4-(4-chlorophenylsulfonylamino)-2-[(Z)-5-sulfino-1-pentenyl]pyrrolidine (350 mg) as a powder.

$^1$H-NMR (CD$_3$OD) δppm: 1.7–2.0 (4H, m), 2.1–2.3 (2H, m), 2.79 (2H, t, J=7.5 Hz), 3.45–3.55 (2H, m), 3.60 (1H, m), 4.42 (1H, q, J=7.0 Hz), 5.3–5.4 (2H, m), 7.5–7.65 (4H, m), 7.7–7.85 (4H, m)

EXAMPLE 31

The following compound was obtained according to a similar manner to that of Example 20(1).

(2S,4R)-1-t-Butoxycarbonyl-2-[(E and Z)-5-carboxy-5,5-difluoro-1-pentenyl]-4-(4-chlorophenylsulfonylamino)pyrrolidine

EXAMPLE 32

The following compound was obtained according to a similar manner to that of Example 21(1).

(2S,4R)-2-[(E and Z)-5-Carboxy-5,5-difluoro-1pentenyl]-4-(4-chlorophenylsulfonylamino)pyrrolidine trifluoroacetate

EXAMPLE 33

The following compound was obtained according to a similar manner to that of Example 22(1).

(2S,4R)-2-[(Z)-5-Carboxy-5,5-difluoro-1-pentenyl]-1-(4-chlorophenylsulfonyl)-4-(4-chlorophenylsulfonylamino)pyrrolidine mp: 145°–147° C.

$^1$H-NMR (CDCl$_3$+CD$_3$OD) δppm: 1.5–1.7 (2H, m), 1.8–2.2 (4H, m), 3.3–3.4 (2H, m) 3.52 (1H m), 4.41 (1H, q, J=8.5 Hz), 5.1–5.4 (2H, m), 7.35–7.45 (4H, m), 7.6–7.7 (4H, m)

EXAMPLE 34

A mixture of (2S,4R)-2-[(Z)-5-bromo-1-pentenyl]-1-(4-chlorophenylsulfonyl)-4-(4-chlorophenylsulfonylamino)pyrrolidine (200 mg) and triethyl phosphite (5.0 ml) was refluxed for 3 hours and evaporated in vacuo to give an oil. The oil was chromatographed on silica gel column with chloroform as an eluent to give (2S,4R)-1-(4-chlorophenylsulfonyl)-4-(4-chlorophenylsulfonylamino)-2-[(Z)-5-diethoxyphosphoryl-1-pentenyl]pyrrolidine (164 mg) as an oil.

$^1$H-NMR (CDCl$_3$) δppm: 1.2–1.4 (6H, m), 1.65–1.85 (4H, m), 2.0–2.3 (4H, m), 3.48 (2H, m), 3.68 (1H, m), 4.0–4.2 (4H, m), 4.57 (1H, q, J=6.5 Hz), 5.2–5.5 (2H, m), 6.50 (1H, d, J=6 Hz), 7.4–7.5 (4H, m) 7.7–7.8 (4H, m)

EXAMPLE 35

To a solution of (2S,4R)-1-(4-chlorophenylsulfonyl)-4-(4-chlorophenylsulfonylamino)-2-[(Z)-5-diethoxyphosphoryl-1-pentenyl]pyrrolidine (146 mg) in dichloromethane (5.0 ml) was added bromotrimethylsilane (0.1 ml) and the mixture was stirred at room temperature for 3 hours. After the mixture was evaporated to dryness, the residue was dissolved in acetone (5 ml), and water (20 μl) was added thereto. The mixture was stirred at room temperature for 1 hour and the solvent was evaporated in vacuo. The residue was solidified with a mixture of chloroform and water to give (2S,4R)-1-(4-chlorophenylsulfonyl)-4-(4-chlorophenylsulfonylamino)-2-[(Z)-5-phosphono-1-pentenyl]pyrrolidine (70 mg) as a powder.

$^1$H-NMR (CD$_3$OD) δppm: 1.6–1.9 (6H, m), 2.1–2.3 (2H, m), 3.4–3.5 (2H, m), 3.63 (1H, m), 4.42 (1H, q, J=7.0 Hz), 5.25–5.45 (2H, m), 7.5–7.6 (4H, m), 7.7–7.8 (4H, m)

EXAMPLE 36

To a solution of (2S,4R)-2-[(Z)-5-carboxy-1-pentenyl]-1-(4-chlorophenylsulfonyl)-4-(4-chlorophenylsulfonylamino)pyrrolidine (274 mg) were added sodium hydride (60 mg) and iodomethane (0.1 ml) and the mixture was stirred at room temperature for 5 hours. The solution was diluted with ethyl acetate and washed successively with water and brine. The organic solution was dried over magnesium sulfate and evaporated in vacuo. The residue was chromatographed on silica gel with a mixture of n-hexane and ethyl acetate (3:1) as an eluent to give (2S,4R)-1-(4-chlorophenylsulfonyl)-4-[N-(4-chlorophenylsulfonyl)-N-methylamino]-2-[(Z)-5-methoxycarbonyl-1-pentenyl]pyrrolidine (220 mg) as an oil.

¹H-NMR (CDCl₃) δppm: 1.6-1.8 (3H, m), 2.02 (1H, m), 2.05 (2H, q, J=7.5 Hz), 2.33 (2H, t, J8 Hz), 2.69 (3H, s), 3.15 (1H, dd, J=7.5, 10 Hz), 3.37 (1H, dd, J=7.5, 10 Hz), 3.68 (3H, s), 4.5-4.8 (2H, m), 5.70 (1H, t, J=10.5 Hz), 5.41 (1H, dt, J=7.5, 10.5 Hz), 7.4-7.6 (4H, m), 7.6-7.8 (4H, m)

EXAMPLE 37

The following compounds were obtained according to similar manners to those of Examples 1 (1), 10 and 20 (1).

(1) (2S,4R)-2-[(Z)-5-Carboxy-5-methyl-1-hexenyl]-1-(4-chlorophenylsulfonyl)-4-(4-chlorophenylsulfonylamino)pyrrolidine
mp: 159°-160° C.

¹H-NMR (CD₃OD) δppm: 1.20 (3H, s), 1.22 (3H, s), 1.5-1.8 (5H, m), 2.0-2.2 (2H, m), 3.43 (1H, m), 3.64 (1H, m), 4.43 (1H, q, J=8 Hz), 5.2-5.4 (2H, m), 7.57 (2H, d, J=7.5 Hz), 7.61 (2H, d, J=7.5 Hz), 7.77 (2H, d, J=7.5 Hz), 7.78 (2H, d, J=7.5 Hz)

(2) (2S,4R)-2-[(Z)-6-Carboxy-1-hexenyl]-1-(4-chlorophenylsulfonyl)-4-(4-chlorophenylsulfonylamino)pyrrolidine
mp: 112°-114° C.

¹H-NMR (CDCl₃+CD₃OD) δppm: 1.3-1.5 (2H, m), 1.5-1.8 (4H, m), 1.93 (1H, m), 2.09 (2H, q, J=7.5 Hz), 2.32 (2H, t, J=7.5 Hz), 3.41 (1H, m), 3.74 (1H, m), 4.52 (1H, q, J=8.5 Hz), 5.50 (1H, dd, J=8.5, 10 Hz), 5.42 (dt, J=7.5, 10 Hz), 7.50 (4H, d, J=8 Hz), 7.71 (2H, d, J=8 Hz), 7.78 (2H, d, J=8 Hz)

(3) (2S,4R)-2-[(Z)-5-Carboxy-1-hexenyl]-1-(4-chlorophenylsulfonyl)-4-(4-chlorophenylsulfonylamino)pyrrolidine
mp: 159°-160° C.

¹H-NMR (CDCl₃+CD₃OD) δppm: 1.12 (3×1/3H, d, J=6.5 Hz), 1.13 (3×2/3H, d, J=6.5 Hz), 1.3-1.5 (2H, m), 1.6-1.8 (2H, m), 1.87 (1H, m), 1.9-2.1 (2H, m), 2.34 (1H, m), 3.3-3.5 (2H, m), 4.42 (1H, q, J=8 Hz), 5.13 (1H, m), 5.34 (1H, m), 7.35-7.45 (4H, m), 7.6-7.7 (4H, m)

(4) 2S,4R)-2-[(E and Z)-5-Carboxy-1-methyl-1-pentenyl]-(4-chlorophenylsulfonyl)-4-(4-chlorophenylsulfonylamino)pyrrolidine
mp: 106°-110° C.

¹H-NMR (CDCl₃) δppm: 1.59 (3H, s), 1.6-1.8 (2H, m), 1.84 (1H, m), 2.0-2.2 (3H, m), 2.38 (2H, t, J=7.0 Hz), 3.18 (1H, m), 3.42 (1H, m), 3.74 (1H, m), 4.45 (1H, t, J=7.0 Hz), 5.22 (1H, m), 5.40 (1H, d, J=7.0 Hz), 7.4-7.5 (4H, m), 7.65-7.8 (4H, m)

(5) (2S,4R)-2-[(Z)-5-Carboxy-1-pentenyl]-1-(4-chlorophenylsulfonyl)-4-(4-methylphenylsulfonylamino)pyrrolidine
mp: 98°-101° C.

¹H-NMR (CDCl₃) δppm: 1.5-1.8 (5H, m), 1.98 (1H, m), 2.1-2.2 (2H, m), 2.43 (3H, s), 3.4-3.5 (2H, m), 3.69 (1H, m), 4.52 (1H, q, J=7.5 Hz), 5.2-5.5 (3H, m), 7.32 (2H, d, J=8 Hz), 7.50 (2H, d, J=8 Hz), 7.68 (2H, d, J=8 Hz), 7.75 (2H, d, J=8 Hz)

(6) (2S,4R)-2-[(Z)-5-Carboxy-1-pentenyl]-1-(4-chlorophenylsulfonyl)-4-(4-methoxyphenylsulfonylamino)pyrrolidine
mp: 90° C.

¹H-NMR (CDCl₃) δppm: 1.5-1.8 (3H, m), 2.02 (1H, m), 2.17 (2H, q, J=7.5 Hz), 2.49 (2H, t, J=6.5 Hz), 3.4-3.5 (2H, m), 3.66 (1H, m), 3.88 (3H, s), 4.50 (1H, q, J=7 Hz), 5.2-5.5 (3H, m), 6.98 (2H, d, J=8 Hz), 7.50 (2H, d, J=8 Hz), 7.75 (4H, d, J=8 Hz)

(7) (2S,4R)-2-[(Z)-5-Carboxy-1-pentenyl]-1-(4-chlorophenylsulfonyl)-4-(4-trifluoromethylphenylsulfonylamino)pyrrolidine mp: 140°-141° C.

¹H-NMR (CDCl₃) δppm: 1.5-1.8 (3H, m), 2.05 (1H, m), 2.18 (2H, q, J=7.5 Hz), 2.40 (2H, t, J=6.5 Hz), 3.41 (dd, J=4.5, 11 Hz), 3.53 (1H, dd, J=3, 11 Hz), 3.79 (1H, m), 4.65 (1H, q, J=7 Hz), 5.22 (1H, dd, J=11, 10 Hz), 5.44 (1H, dt, J=11, 7.5 Hz), 5.78 (1H, d, J=6.5 Hz), 7.45 (2H, d, J=8 Hz), 7.72 (2H, d, J=8 Hz), 7.89 (2H, d, J=8 Hz), 7.98 (2H, d, J=8 Hz)

(8) (2S,4R)-2-[(Z)-5-Carboxy-1-pentenyl]-4-(4-chlorophenylsulfonylamino)-1-(2-thienylsulfonyl)pyrrolidine mp: 115°-116° C.

¹H-NMR (CDCl₃+CD₃OD) δppm: 1.5-2.0 (4H, m), 2.15 (2H, q, J=7 Hz), 2.33 (2H, t, J=7.5 Hz), 3.3-3.6 (2H, m), 3.68 (1H, m), 4.52 (1H, q, J=8 Hz), 5.3-5.5 (2H, m), 7.17 (1H, dd, J=3, 5 Hz), 7.50 (2H, d, J=8.5 Hz), 7.60 (1H, m), 7.66 (1H, m), 7.75 (2H, d, J=8.5 Hz)

(9) (2S,4R)-2-[(Z)-5-Carboxy-1-pentenyl]-1-(4-chlorophenylsulfonyl)-4-[N-(4-chlorophenylsulfonyl)N-methylamino]pyrrolidine
mp: 90°-92° C.

¹H-NMR (CDCl₃) δppm: 1.6-1.8 (3H, m), 2.02 (1H, dt, J=8.5, 12.5 Hz), 2.18 (2H, q, J=7.5 Hz), 2.37 (2H, t, J=8 Hz), 2.68 (3H, s), 3.13 (1H, dd, J=7.5, 10 Hz), 3.37 (1H, dd, J=7.5, 10 Hz), 4.5-4.7 (2H, m), 5.22 (1H, t, J=10.5 Hz), 5.40 (1H, dt, J=7.5, 10.5 Hz), 7.45-7.55 (4H, m), 7.65-7.75 (4H, m)

(10) (2S,4R)-2-[(Z)-5-Carboxy-5,5-difluoro-1-pentenyl]--(4-chlorophenylsulfonyl)-4-(4-chlorophenylsulfonylamino)pyrrolidine
mp: 145°-147° C.

¹H-NMR (CDCl₃+CD₃OD) δppm: 1.5-1.7 (2H, m), 1.8-2.2 (4H, m), 3.3-3.4 (2H, m), 3.52 (1H, m), 4.41 (1H, q, J=8.5 Hz), 5.1-5.4 (2H, m), 7.35-7.45 (4H, m), 7.6-7.7 (4H, m)

What we claim is:

1. A compound of the formula:

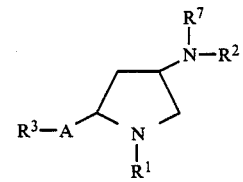

wherein R¹ is hydrogen, lower alkoxycarbonyl, phenylsulfonyl, phenylsulfonyl substituted with 1 to 3 substituent(s) selected from the group consisting of halogen, nitro, lower alkoxy, mono (or di or tri)halo(lower)alkyl and lower alkyl, phenylcarbamoyl, lower alkylsulfonyl, benzoyl or thienylsulfonyl;

R² is phenylsulfonyl or phenylsulfonyl substituted with 1 to 3 substituent(s) selected from the group consisting of halogen, lower alkyl, lower alkoxy and mono(or di or tri)halo(lower)alkyl, R³ is carboxy(lower)alkyl, lower alkyl substituted with carboxy and 1 to 3 halogen atom(s), esterified carboxy(lower)alkyl, carbamoyl(lower)alkyl, lower alkylsulfonylcarbamoyl(lower)alkyl, phenylsulfonylcarbamoyl(lower)alkyl, carboxyphenyl, esterified carboxyphenyl, carboxy, esterified carboxy, hydroxy(lower)alkyl, sulfino(lower)alkyl, phosphono(lower)alkyl, di(lower)alkoxyphosphoryl(lower)alkyl or halo(lower)alkyl, $R^7$ is hydrogen or lower alkyl, and
A is $$-CH=\underset{R^8}{C}- \text{ or } -CH_2-\underset{R^8}{CH}-$$

in which $R^8$ is hydrogen or lower alkyl, or a pharmaceutically acceptable salt thereof.

2. A compound of the formula:

wherein $R^1$ is hydrogen, lower alkoxycarbonyl, phenylsulfonyl, phenylsulfonyl substituted with 1 to 3 substituent(s) selected from the group consisting of halogen, nitro, lower alkoxy, mono(or di or tri)halo(lower)alkyl and lower alkyl, phenylcarbamoyl, lower alkylsulfonyl, benzoyl or thienylsulfonyl;

$R^2$ is phenylsulfonyl or phenylsulfonyl substituted with 1 to 3 substituent(s) selected from the group consisting of halogen, lower alkyl, lower alkoxy and mono(or di or tri)halo(lower)alkyl, $R^7$ is hydrogen, or lower alkyl, and $R^8$ is hydrogen or lower alkyl, or a pharmaceutically acceptable salt thereof.

3. A compound of claim 1, wherein $R^3$ is carboxy(lower)alkyl, lower alkyl substituted with carboxy and one or two halogen atom(s), lower alkoxycarbonyl(lower)alkyl, carbamoyl(lower)alkyl, lower alkylsulfonylcarbamoyl(lower) alkyl, phenysulfonylcarbamoyl(lower)alkyl, carboxyphenyl, lower alkoxycarbonylphenyl, carboxy, lower alkoxycarbonyl, hydroxy(lower)alkyl, sulfino(lower)alkyl, phosphono(lower)alkyl, di(lower)alkoxyphosphoryl(lower)alkyl or halo(lower)alkyl.

4. A compound of claim 3, wherein $R^1$ is hydrogen, lower alkoxycarbonyl, phenylsulfonyl, phenylsulfonyl substituted with one substituent selected from the group consisting of halogen, nitro, lower alkoxy, mono (or di or tri)halo(lower)alkyl and lower alkyl, phenylcarbamoyl, lower alkylsulfonyl, benzoyl or thienylsulfonyl; and $R^2$ is phenylsulfonyl or phenylsulfonyl substituted with one substituent selected from the group consisting of halogen, lower alkyl, lower alkoxy and mono(or di or tri)halo(lower)alkyl.

5. A compound of claim 4, wherein $R^1$ is hydrogen, phenylsulfonyl, phenylsulfonyl substituted with one substituent selected from the group consisting of halogen, nitro, lower alkoxy, mono(or di or tri)halo(lower)alkyl and lower alkyl, $R^2$ is phenylsulfonyl or phenylsulfonyl substituted with one substituent selected from the group consisting of halogen, lower alkyl, lower alkoxy and mono(or di or tri)halo(lower)alkyl, $R^3$ is carboxy(lower)alkyl, $R^7$ is hydrogen or lower alkyl, and A is $$-CH=\underset{R^8}{C}-$$

(in which $R^8$ is hydrogen or lower alkyl).

6. A compound of claim 5, wherein $R^1$ is phenylsulfonyl substituted with one halogen, $R^2$ is phenylksulfonyl substituted with on halogen, $R^7$ is hydrogen, and A is $-CH=CH-$.

7. A compound of claim 6, which is (2S,4R)-2-[(Z)-5-carboxy-1-pentenyl]-1-(4-chlorophenylsulfonyl)-4-(4-chlorophenylsulfonylamino)pyrrolidine.

8. A thromboxane $A_2$ ontagonist pharmaceutical composition which comprises, an effective amount of a compound of claim 1 in admixture with a pharmaceutically acceptable carrier.

9. A method for the treatment of thrombosis, asthma or nephritis which comprises administering an effective amount of a compound of claim 1 to a human or animals.

* * * * *